(12) United States Patent
Krarup et al.

(10) Patent No.: US 11,155,583 B2
(45) Date of Patent: Oct. 26, 2021

(54) STABILIZED SOLUBLE PRE-FUSION RSV F PROTEINS

(71) Applicant: Janssen Vaccines & Prevention B.V., Leiden (NL)

(72) Inventors: Anders Krarup, Glostrup (DK); Johannes Petrus Maria Langedijk, Amsterdam (NL)

(73) Assignee: Janssen Vaccines & Prevention B.V., Leiden (NL)

( * ) Notice: Subject to any disclaimer, the term of this patent is extended or adjusted under 35 U.S.C. 154(b) by 0 days.

(21) Appl. No.: 16/091,344

(22) PCT Filed: Apr. 4, 2017

(86) PCT No.: PCT/EP2017/057962
§ 371 (c)(1),
(2) Date: Oct. 4, 2018

(87) PCT Pub. No.: WO2017/174568
PCT Pub. Date: Oct. 12, 2017

(65) Prior Publication Data
US 2019/0119330 A1    Apr. 25, 2019

(30) Foreign Application Priority Data
Apr. 5, 2016  (EP) ..................................... 16163810

(51) Int. Cl.
| | |
|---|---|
| *A61K 39/12* | (2006.01) |
| *C07K 14/135* | (2006.01) |
| *C07K 14/005* | (2006.01) |
| *A61P 31/14* | (2006.01) |
| *C07K 16/10* | (2006.01) |
| *C12N 15/62* | (2006.01) |
| *A61K 39/00* | (2006.01) |

(52) U.S. Cl.
CPC ............ *C07K 14/135* (2013.01); *A61K 39/12* (2013.01); *A61P 31/14* (2018.01); *C07K 14/005* (2013.01); *C07K 16/1027* (2013.01); *C12N 15/62* (2013.01); *A61K 2039/55505* (2013.01); *A61K 2039/57* (2013.01); *C12N 2760/18522* (2013.01); *C12N 2760/18534* (2013.01)

(58) Field of Classification Search
None
See application file for complete search history.

(56) References Cited

U.S. PATENT DOCUMENTS

| | | |
|---|---|---|
| 4,235,877 A | 11/1980 | Fullerton |
| 4,372,945 A | 2/1983 | Likhite |
| 4,474,757 A | 10/1984 | Arnon et al. |
| 5,057,540 A | 10/1991 | Kensil et al. |
| 5,122,458 A | 6/1992 | Post et al. |
| 5,385,839 A | 1/1995 | Stinski |
| 5,559,099 A | 9/1996 | Wickham et al. |
| 5,837,511 A | 11/1998 | Falck-Pedersen et al. |
| 5,837,520 A | 11/1998 | Shabram et al. |
| 5,846,782 A | 12/1998 | Wickham et al. |
| 5,851,806 A | 12/1998 | Kovesdi et al. |
| 5,891,690 A | 4/1999 | Massie |
| 5,965,541 A | 10/1999 | Wickham et al. |
| 5,981,225 A | 11/1999 | Kochanek et al. |
| 5,994,106 A | 11/1999 | Kovesdi et al. |
| 5,994,128 A | 11/1999 | Fallaux et al. |
| 6,020,191 A | 2/2000 | Scaria et al. |
| 6,040,174 A | 3/2000 | Imler et al. |
| 6,083,716 A | 7/2000 | Wilson et al. |
| 6,113,913 A | 9/2000 | Brough et al. |
| 6,225,289 B1 | 5/2001 | Kovesdi et al. |
| 6,261,823 B1 | 7/2001 | Tang et al. |
| 6,485,958 B2 | 11/2002 | Blanche et al. |
| 7,270,811 B2 | 9/2007 | Bout et al. |
| 7,326,555 B2 | 2/2008 | Konz, Jr. et al. |
| 8,772,256 B2 | 7/2014 | Graham et al. |
| 8,932,607 B2 | 1/2015 | Custers et al. |
| 2011/0305727 A1 | 12/2011 | Swanson et al. |
| 2012/0164176 A1 | 6/2012 | Swanson et al. |
| 2012/0315270 A1 | 12/2012 | McLellan et al. |
| 2013/0177573 A1 | 7/2013 | Williamson et al. |
| 2014/0073032 A1 | 3/2014 | Custers et al. |
| 2014/0248314 A1 | 9/2014 | Swanson et al. |
| 2014/0271699 A1 | 9/2014 | Kwong et al. |
| 2016/0102123 A1 | 4/2016 | Langedijk et al. |
| 2016/0145321 A1 | 5/2016 | Wadia et al. |
| 2016/0145322 A1 | 5/2016 | Wadia et al. |
| 2016/0176932 A1 | 6/2016 | Langedijk et al. |
| 2020/0197509 A1 | 6/2020 | Widjojoatmodjo |

FOREIGN PATENT DOCUMENTS

| | | |
|---|---|---|
| EP | 0853660 A1 | 7/1998 |
| EP | 1230354 | 8/2002 |
| WO | 9003184 A1 | 4/1990 |

(Continued)

OTHER PUBLICATIONS

McClellan et al., Science vol. 340, p. 1114, (Year: 2013).*
McClellan et al (Science vol. 342, p. 592ff, 2013 (Year: 2013).*
Gilman et al., "Rapid profiling of RSV antibody repertories from the memory B cells of naturally infected adult donors", Science Immunology, 11 pages, Dec. 2016.

(Continued)

*Primary Examiner* — Shanon A. Foley
*Assistant Examiner* — Myron G Hill
(74) *Attorney, Agent, or Firm* — Ice Miller LLP

(57) ABSTRACT

Stable pre-fusion respiratory syncitial virus (RSV) F proteins (or fragment thereof) are described. Compositions containing the proteins and uses of the compositions for the prevention and/or treatment of RSV infection are also described.

19 Claims, 14 Drawing Sheets

Specification includes a Sequence Listing.

(56) References Cited

FOREIGN PATENT DOCUMENTS

| | | | |
|---|---|---|---|
| WO | 9014837 A1 | 12/1990 | |
| WO | 96/09378 A1 | 3/1996 | |
| WO | 9611711 A1 | 4/1996 | |
| WO | 98/22588 A2 | 5/1998 | |
| WO | 98/39411 A1 | 9/1998 | |
| WO | 99/12568 A1 | 3/1999 | |
| WO | 99/41416 A2 | 8/1999 | |
| WO | 2000/29024 A1 | 5/2000 | |
| WO | 2000/32754 A1 | 6/2000 | |
| WO | 2000/70071 A1 | 11/2000 | |
| WO | 2001/66137 A1 | 9/2001 | |
| WO | 2001085984 A1 | 11/2001 | |
| WO | 2002/40665 A2 | 5/2002 | |
| WO | 03040178 A1 | 5/2003 | |
| WO | 2003/049763 A1 | 6/2003 | |
| WO | 2003/061708 A1 | 7/2003 | |
| WO | 2003/078592 A2 | 9/2003 | |
| WO | 2003/104467 A1 | 12/2003 | |
| WO | 2004001032 A2 | 12/2003 | |
| WO | 2004004762 A1 | 1/2004 | |
| WO | 2004/020971 A2 | 3/2004 | |
| WO | 2005002620 A1 | 1/2005 | |
| WO | 2005071093 A2 | 8/2005 | |
| WO | 2005/080556 A2 | 9/2005 | |
| WO | 2006/108707 A1 | 10/2006 | |
| WO | 2007/104792 A2 | 9/2007 | |
| WO | 2007/110409 A1 | 10/2007 | |
| WO | 2009/11713 A1 | 1/2009 | |
| WO | 2009079796 A1 | 7/2009 | |
| WO | 2010/060719 A1 | 6/2010 | |
| WO | 2010086189 A2 | 8/2010 | |
| WO | 2010149743 A2 | 12/2010 | |
| WO | 2010149745 A1 | 12/2010 | |
| WO | 2011008974 A2 | 1/2011 | |
| WO | 2011/020079 A1 | 2/2011 | |
| WO | 2011/045378 A1 | 4/2011 | |
| WO | 2011/045381 A1 | 4/2011 | |
| WO | 2011050168 A2 | 4/2011 | |
| WO | 2011/098592 A1 | 8/2011 | |
| WO | 2012006596 A2 | 1/2012 | |
| WO | 2012158613 A1 | 11/2012 | |
| WO | 2013/139911 A1 | 9/2013 | |
| WO | 2013/139916 A1 | 9/2013 | |
| WO | 2013135615 A1 | 9/2013 | |
| WO | 2014005643 A1 | 1/2014 | |
| WO | 2014160463 A1 | 10/2014 | |
| WO | 2014174018 A1 | 10/2014 | |
| WO | WO-2014174018 A1 * | 10/2014 | ........... C07K 14/005 |
| WO | 2014202570 A1 | 12/2014 | |
| WO | 2015013551 A1 | 1/2015 | |
| WO | 2015040002 A1 | 3/2015 | |
| WO | 2017174564 A1 | 10/2017 | |

OTHER PUBLICATIONS

Openshaw et al., "Protective and Harmful Immunity to RSV Infection", Annu Rev. Immunol, vol. 35, pp. 501-532, 2017.
Janssen Vaccines & Prevention B.V.: A Study to Evaluate the Safety, Tolerability and Immunogenicity of Two Vaccinations of Ad26.RSV. preF One Year Apart in Adults Aged 60 Years and Older in Stable Health, Oct. 2016, retrieved from the Internet: http://clinicaltrials.gov/ct2/show/record/NCT02926430 (retrived on Nov. 30, 2018.
Int'l Search Report and Written Opinion dated Dec. 17, 2018 in Int'l Application No. PCT/EP2018/074710.
Mclellan et al., "Structural Basis of Respiratory Syncytial Virus Neutralization by Motavizumab," Nature Structural & Molecular Biology, vol. 17, pp. 248-250 (2010).
Mclellan et al., "Structure of RSV Fusion Glycoprotein Trimer Bound to a Prefusion-Specific Neutralizing Antibody," Science, vol. 340, pp. 1113-1117 (2013).
Mclellan et al., "Structure-Based Design of a Fusion Glycoprotein Vaccine for Respiratory Syncytial Virus," Science, vol. 342, pp. 592-598 (2013).
Swanson et al., "Structural Basis for Immunization with Postfusion Respiratory Syncytial Virus Fusion F Glycoprotein (RSV F) to Elicit High Neutralizing Antibody Titers," PNAS, vol. 108, pp. 9619-9624 (2011).
Letarov et al., "The Carboxy-Terminal Domain Initiates Trimerization of Bacteriophage T4 Fibritin," Biochemistry (Moscow), vol. 64, No. 7, pp. 817-823 (1999).
Guthe et al., "Very Fast Folding and Association of a Trimerization Domain from Bacteriophage T4 Fibritin," J. Mol. Biol., vol., 337, pp. 905-915 (2004).
"Database UniProt Accession W8CJC7," http://ibis.internal.epo.org/exam/dbfetch.jsp?id=UNIPROT:W8CJC7, Download date: Aug. 12, 2015, 1 page.
Widjaja et al., "Recombinant soluble Respiratory Syncytial Virus F Protein That Lacks Heptad Repeat B, Contains a GCN4 Trimerization Motif and Is Not Cleaved Displays Prefusion-Like Characteristics," PLOS ONE, 20 pages, Jun. 24, 2015.
Written Opinion dated Oct. 10, 2016 in Int'l Application No. PCT/EP2016/066104.
Int'l Search Report dated Oct. 10, 2016 in Int'l Application No. PCT/EP2016/066104.
Written Opinion dated Oct. 12, 2016 in Int'l Application No. PCT/EP2016/066098.
Int'l Search Report dated Oct. 12, 2016 in Int'l Application No. PCT/EP2016/066098.
Suzuki et al., "An Isoleucine Zipper Peptide Forms a Native-like Triple Stranded Coiled Coil in Solution," Protein Engineering, vol. 11, No. 11, pp. 1051-1055 (1998).
Dames et al., "NMR Structure of a Parallel Homotrimeric Coiled Coil," Nature Structural Biology, vol. 5, No. 8, pp. 687-691 (Aug. 1998).
Calder et al., "Electron Microscopy of the Human Respiratory Syncytial Virus Fusion Protein and Complexes That It Forms With Monoclonal Antibodies," Virology, vol. 271, pp. 122-131 (2000).
Harbury et al., "A Switch Between Two-, Three-, and Four-Stranded Coiled Coils in GCN4 Leucine Zipper Mutants," Science, vol. 262, pp. 1401-1407.
O'Shea et al., "Evidence That the Leucine Zipper Is a Coiled Coil," Science, vol. 243, pp. 538-542 (Jan. 27, 1989).
Database EMBL, Aug. 28, 1995, Human respiratory syncytial virus, strain RSB89-1734, fusion protein (F) mRNA, ,complete CDS, XP002729919.
Int'l Search Report and Written Opinion dated Oct. 9, 2014 in Int'l Application No. PCT/EP2014/062655.
Int'l Search Report and Written Opinion dated Aug. 12, 2014 in Int'l Application No. PCT/EP2014/058353.
Magro et al., "Neutralizing Antibodies Against the Preactive Form of Respiratory Syncytial Virus Protein Offer Unique Possibilities for Clinical Intervention," PNAS, vol. 109, No. 8, pp. 3089-3094 (Feb. 21, 2012).
Yin et al., "Structure of the Parainfluenza Virus 5 F Protein in its Metastable, Prefusion Conformation," Nature, vol. 439, pp. 38-44 (Jan. 5, 2006).
Ngwuta et al, "Prefusion F-Specific Antibodies Determine the Magnitude of RSV Neutralizing Activity in Human Sera," Science Translational Medicine, vol. 7, No. 309, pp. 1-9 (2015).
Int'l Search Report and Written Opinion dated Jun. 12, 2017 in Int'l Application No. PCT/EP2017/057962.
Abbink et al, "Comparative Seroprevalence and Immunogenicity of Six Rare Serotype Recombinant Adenovirus Vaccine Vectors from Subgroups B and D," Journal of Virology, vol. 81, No. 9, pp. 4654-4663 (May 2007).
Abrahamsen et al, "Construction of an Adenovirus Type 7a E1A-Vector," Journal of Virology, vol. 71, No. 11, pp. 8946-8951 (Nov. 1997).
Altaras et al, "Production and Formulation of Adenovirus Vectors," Advances in Biochemical Engineering / Biotechnology, vol. 99, pp. 193-260 (2005).
Brough et al, "A Gene Transfer Vector-Cell Line System for Complete Functional Complementation of Adenovirus Early Regions E1 and E4," Journal of Virology, vol. 70, No. 9, pp. 6497-6501 (Sep. 1996).

(56) References Cited

OTHER PUBLICATIONS

Fallaux et al, "New Helper Cells and Matched Early Region 1-Deleted Adenovirus Vectors Prevent Generation of Replication-Competent Adenoviruses," Human Gene Therapy, vol. 9, pp. 1909-1917 (Sep. 1998).
Gao et al, "A Cell Line for High-Yield Production of E1-Deleted Adenovirus Vectors without the Emergence of Replication-Competent Virus," Human Gene Therapy, vol. 11, pp. 213-219 (Jan. 2000).
Goerke et al, "Development of a Novel Adenovirus Purification Process Utilizing Selective Precipitation of Cellular DNA," Biotechnology and Bioengineering, vol. 91, pp. 12-21 (2005).
Havenga et al, "Novel replication-incompetent adenoviral B-group vectors: high vector stability and yield in PER.C6 cells," Journal of General Virology, vol. 87, pp. 2135-2143 (2006).
Hoganson et al, "Development of a Stable Adenoviral Vector Formulation," BioProcessing Journal, vol. 1, No. 1, pp. 43-48 (Mar. 2002).
Kim et al, "Single mucosal immunization of recombinant adenovirus-based vaccine expressing F1 protein fragment induces protective mucosal immunity against respiratory syncytial virus infection," Vaccine, vol. 28, pp. 3801-3808 (2010).
Kohlmann et al, "Protective Efficacy and Immunology of an Adenoviral Vector Vaccine Encoding the Codon-Optimized F Protein of Respiratory Syncytial Virus," Journal of Virology, vol. 83, No. 23, pp. 12601-12610 (Dec. 2009).
Konz et al, "Serotype Specificity of Adenovirus Purification Using Anion-Exchange Chromatography," Human Gene Therapy, vol. 16, pp. 1346-1353 (Nov. 2005).
Konz et al, "Scaleable Purification of Adenovirus Vectors," Methods in Molecular Biology, vol. 434, No. 2, pp. 13-23 (2008).
Krarup et al, "A Highly Stable Prefusion RSV F Vaccine Derived from Structural Analysis of the Fusion Mechanism," Nature Communications, vol. 6, pp. 1-11 (Sep. 2015).
Nan et al, "Development of an Ad7 cosmid system and generation of an Ad7DeltaE1DeltaE3HIVMN env/rev recombinant virus," Gene Therapy, vol. 10, pp. 326-336 (2003).
Pemberton et al, "Cytoxic T Cell Specificity for Respiratory Syncytial Virus Proteins: Fusion Protein is an Important Target Antigen," Journal of General Virology, vol. 68, pp. 2177-2182 (1987).
Solabomi et al, "The Oligomerization Domain of C4-Binding Protein (C4bp) Acts as an Adjuvant, and the Fusion Protein Comprised of the 19-Kilodalton Merozoite Surface Protein 1 Fused with the Murine C4bp Domain Protects Mice against Malaria," Infection and Immunity, vol. 76, No. 8, pp. 3817-3823 (Aug. 2008).
Vogels et al, "Replication-Deficient Human Adenovirus Type 35 Vectors for Gene Transfer and Vaccination: Efficient Human Cell Infection and Bypass of Preexisting Adenovirus Immunity," Journal of Virology, vol. 77, No. 15, pp. 8263-8271 (Aug. 2003).
Yu et al, "Single Intranasal Immunization with Recombinant Adenovirus-Based Vaccine Induces Protective Immunity against Respiratory Syncytial Virus Infection," Journal of Virology, vol. 82, No. 5, pp. 2350-2357 (Mar. 2008).
Int'l Search Report and Written Opinion issued Jun. 12, 2017 in Int'l Application No. PCT/EP2017/057957.
Krause et al, "A Broadly Neutralizing Human Monclonal Antibody That Recognizes a Conserved, Novel Epitope on the Globular Head of the Influenza H1N1 Virus Hemagglutinin," Journal of Virology, vol. 85, No. 20, pp. 10905-10908 (Oct. 2011).
Mclellan et al, "Structure of Respiratory Syncytial Virus Fusion Glycoprotein in the Postfusion Conformation Reveals Preservation of Neutralizing Epitopes," Journal of Virology, vol. 85, No. 15, pp. 7788-7796 (Aug. 2011).
Database Geneseq (online) "RSV fusion protein N67I S215P, RSV CL57-v224, fibritin, SEQ: 74", XP002761983, retrieved from EBI accession No. GSP:BBP75438, Database accession No. BBP75438 sequence.
Neuzil, "Progress toward a Respiratory Syncytial Virus Vaccine", Clinical and Vaccine Immunology, vol. 23, pp. 186-188, 2016.
Bangari et al., "Development of nonhuman adenoviruses as vaccine vectors", Vaccine, 24(7), pp. 849-862, 2006.
Cohen et al., "Chimpanzee adenovirus CV-68 adapted as a gene delivery vector interacts with the coxsackievirus and adenovirus receptor", Journal of General Virology, 83, pp. 151-155, 2002.
Farina et al., "Replication-Defective Vector Based on a Chimpanzee Adenovirus", Journal of Virology, vol. 75, No. 23, pp. 11603-11613, Dec. 2001.
Kobinger et al., "Chimpanzee adenovirus vaccine protects against Zaire Ebola Virus", Science Direct, Virology, 346, pp. 394-401, 2006.
Lasaro et al., "New Insights on Adenovirus as Vaccine Vectors", Molecular Therapy, vol. 17, No. 8, pp. 1333-1339, Aug. 2009.
Tatsis et al., "A CD46-binding Chimpanzee Adenovirus Vector as a Vaccine Carrier", American Society of Gene Therapy, vol. 15, No. 3, pp. 608-617, Mar. 2007.
Widjojatomodjo et al., "Recombianant Low-seroprevalent adenoviral vectors Ad26 and Ad35 expressing the respiratory syncytial virus (RSV) fusion protein induce protective immunity against RSV infection in cotton rats", Vaccine, 33, pp. 5406-5414, 2015.
Green et al., "Safety and Immunogenicity of novel respiratory syncytial virus (RSV) vaccines based on the RSV viral proteins F, N and M2-1 encoded by simian adenovirus (PanAd3-RSV) and MVA (MVA-RSV): protocol for an open-label, dose-escalation, single-centre, phase 1 clinical trial in healthy adults", BMJ Open, 13 pages, Oct. 2015.
Grunwald et al., "Novel Vaccine Regimen Elicits Strong Airway Immune Responses and Control of Respiratory Syncytial Virus in Nonhuman Primates", Journal of Virology, vol. 88, No. 8, pp. 3997-4007, Apr. 2014.
Int'l Search Report and Written Opinion dated Sep. 8, 2018 in Int'l Application No. PCT/EP2018/062604.
Comparison to Sequence 16, U.S. Appl. No. 12/517,194; U.S. Pat. No. 8,772,256 (Year: 2014) 4 pages.
International Search Report and Written Opinion issued in PCT/EP2017/062875, dated Aug. 14, 2017, 10 pages.
Hotard et al., "Identification of Residues in the Human Respiratory Syncytial Virus Fusion Protein That Modulate Fusion Activity and Pathogenesis", Journal of Virology, Jan. 2015, vol. 89, No. 1, pp. 512-522.

\* cited by examiner

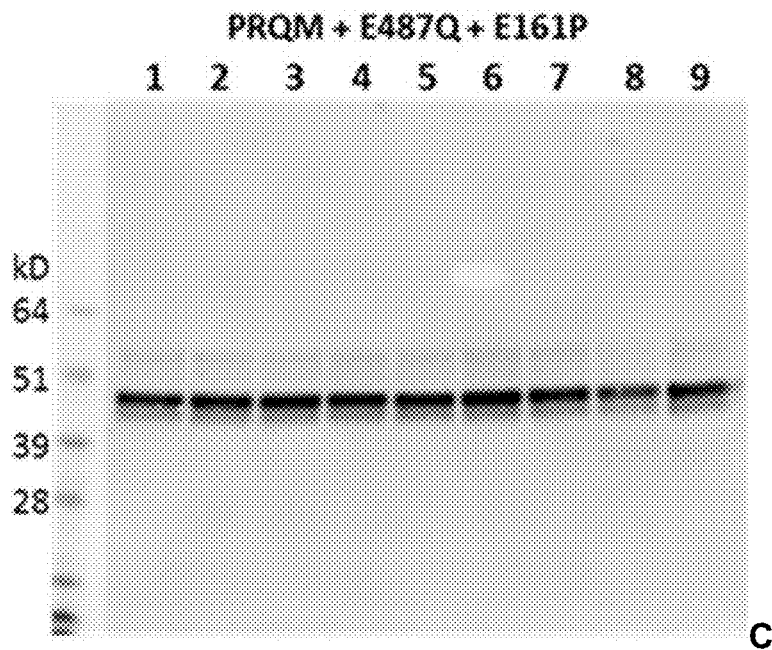
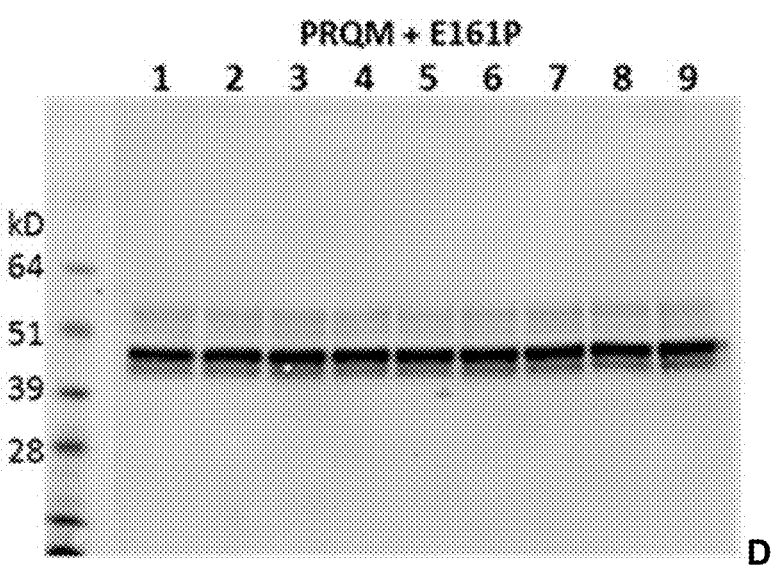
FIG. 6 - continued

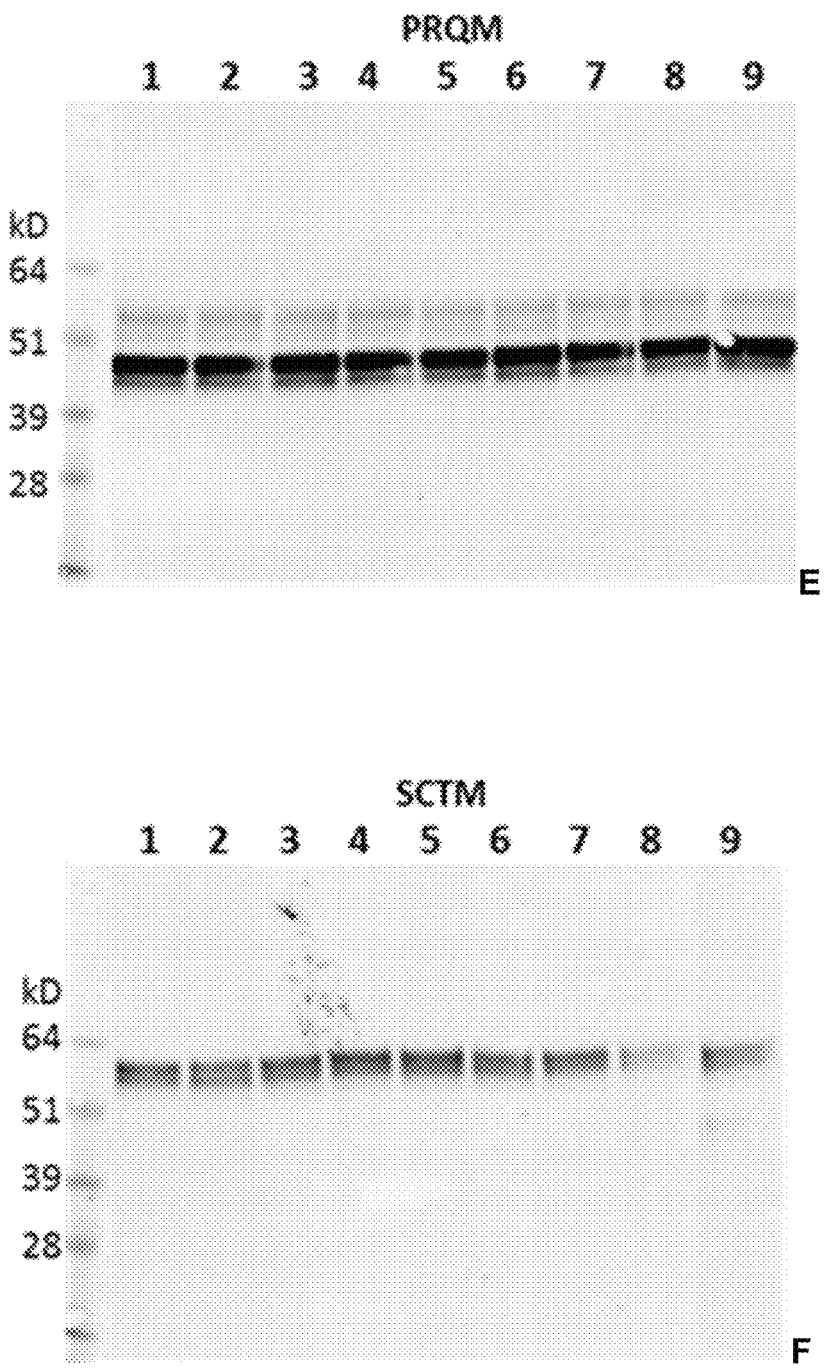
FIG. 6 - continued

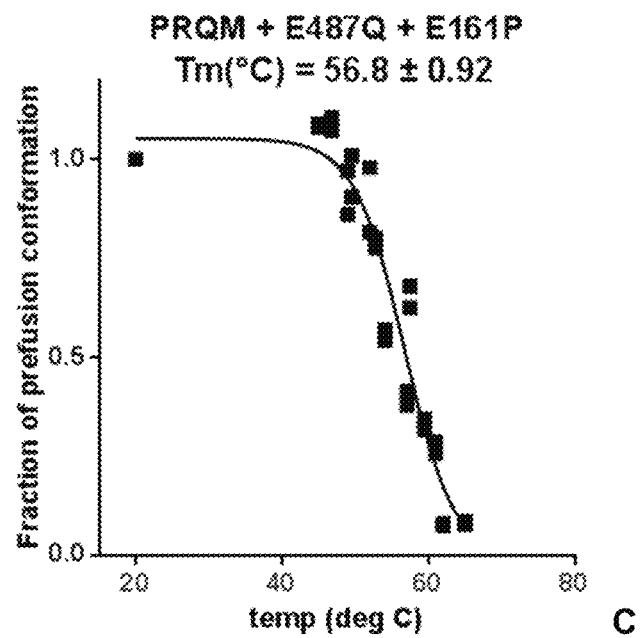
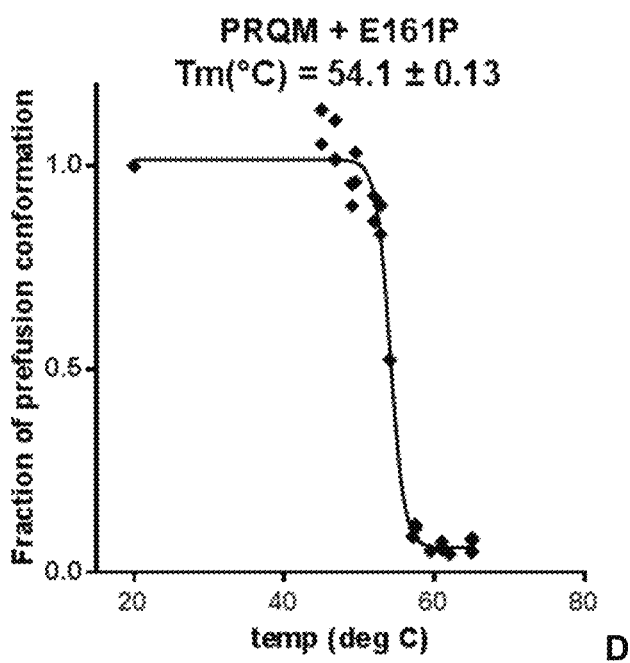
FIG 7. - continued

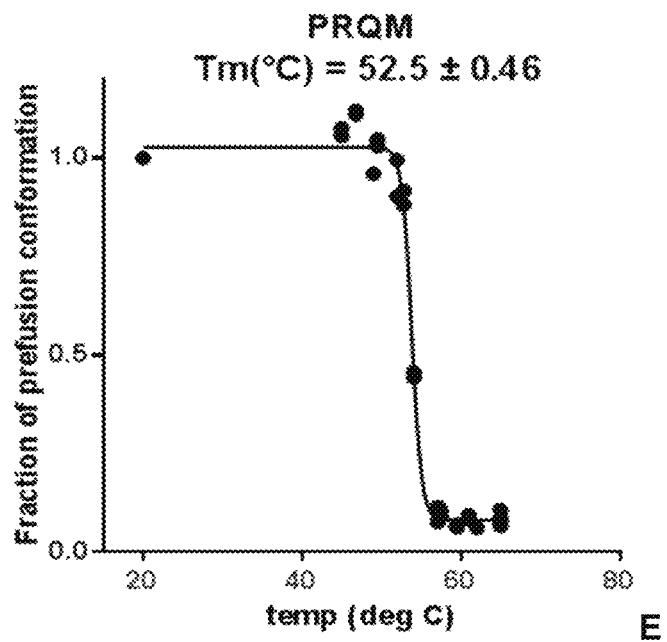
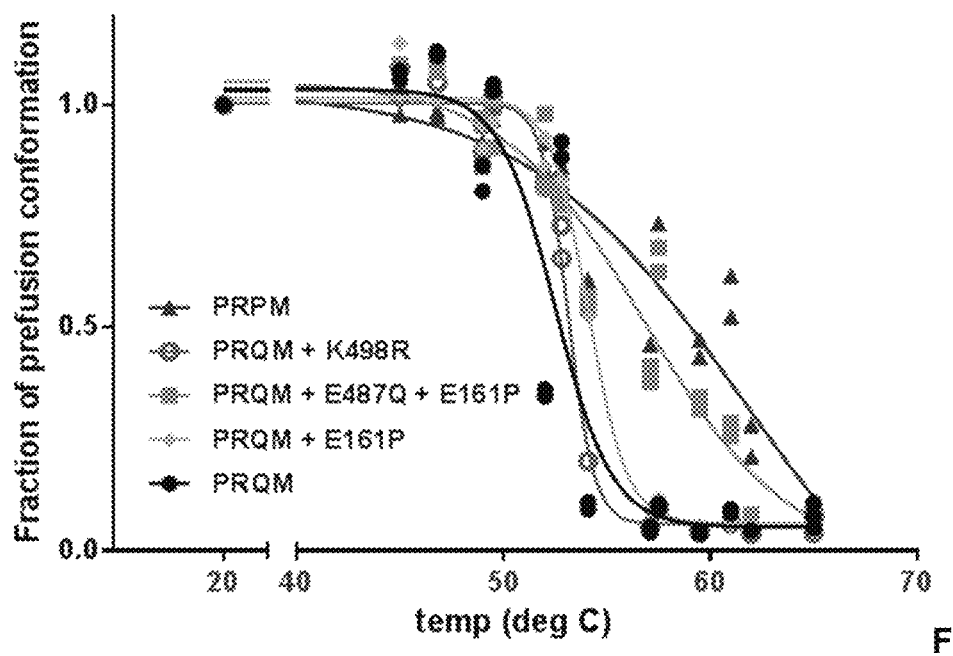
FIG 7. - continued

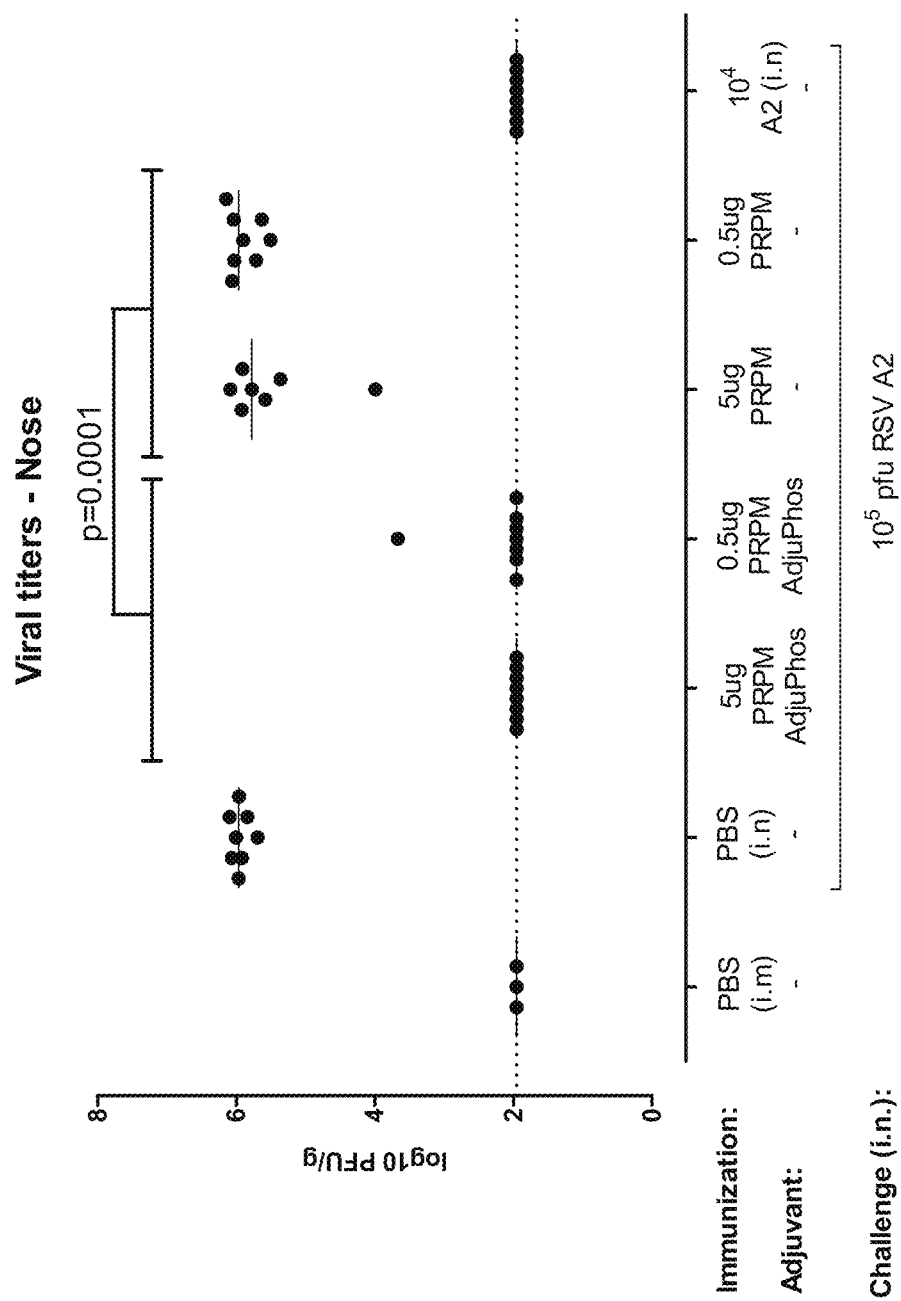
FIG. 8 – continued

SEQUENCE LISTING

<160> NUMBER OF SEQ ID NOS: 22

<210> SEQ ID NO 1
<211> LENGTH: 544
<212> TYPE: PRT
<213> ORGANISM: Artificial Sequence
<220> FEATURE:
<223> OTHER INFORMATION: PRPM

<400> SEQUENCE: 1

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile

-continued

```
            50                  55                  60
Lys Glu Ile Lys Cys Asn Gly Thr Asp Ala Lys Val Lys Leu Ile Lys
 65                  70                  75                  80

Gln Glu Leu Asp Lys Tyr Lys Asn Ala Val Thr Glu Leu Gln Leu Leu
                 85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
            115                 120                 125

Leu Ser Lys Lys Arg Lys Arg Arg Phe Leu Gly Phe Leu Leu Gly Val
            130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
                180                 185                 190

Leu Asp Leu Lys Asn Tyr Ile Asp Lys Gln Leu Leu Pro Ile Val Asn
            195                 200                 205

Lys Gln Ser Cys Ser Ile Pro Asn Ile Glu Thr Val Ile Glu Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
            275                 280                 285

Met Ser Ile Ile Lys Glu Glu Val Leu Ala Tyr Val Val Gln Leu Pro
            290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
            355                 360                 365

Thr Met Asn Ser Leu Thr Leu Pro Ser Glu Val Asn Leu Cys Asn Val
            370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
            450                 455                 460

Lys Ser Leu Tyr Val Lys Gly Glu Pro Ile Ile Asn Phe Tyr Asp Pro
465                 470                 475                 480
```

```
Leu Val Phe Pro Ser Asn Glu Phe Asp Ala Ser Ile Ser Gln Val Asn
            485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
            515                 520                 525

Ala Tyr Val Arg Lys Asp Gly Glu Trp Val Leu Leu Ser Thr Phe Leu
            530                 535                 540

<210> SEQ ID NO 2
<211> LENGTH: 544
<212> TYPE: PRT
<213> ORGANISM: Artificial Sequence
<220> FEATURE:
<223> OTHER INFORMATION: PRQM

<400> SEQUENCE: 2

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Ile Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Pro Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300
```

```
Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
            325                 330                 335

Thr Asp Arg Gly Trp Tyr Cys Asp Asn Ala Gly Ser Val Ser Phe Phe
        340                 345                 350

Pro Gln Ala Glu Thr Cys Lys Val Gln Ser Asn Arg Val Phe Cys Asp
    355                 360                 365

Thr Met Asn Ser Leu Thr Leu Pro Ser Glu Val Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
        515                 520                 525

Ala Tyr Val Arg Lys Asp Gly Glu Trp Val Leu Leu Ser Thr Phe Leu
    530                 535                 540

<210> SEQ ID NO 3
<211> LENGTH: 544
<212> TYPE: PRT
<213> ORGANISM: Artificial Sequence
<220> FEATURE:
<223> OTHER INFORMATION: PRPM + S46G

<400> SEQUENCE: 3

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Gly Ala Leu
            35                  40                  45

Arg Thr Gly Trp Tyr Thr Ser Val Ile Thr Ile Glu Leu Ser Asn Ile
        50                  55                  60

Lys Glu Ile Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125
```

```
Leu Ser Lys Lys Arg Lys Arg Arg Phe Leu Gly Phe Leu Leu Gly Val
            130                 135                 140
Gly Ser Ala Ile Ala Ser Gly Val Ala Val Ser Lys Val Leu His Leu
145                 150                 155                 160
Glu Gly Glu Val Asn Lys Ile Lys Ser Ala Leu Leu Ser Thr Asn Lys
                165                 170                 175
Ala Val Val Ser Leu Ser Asn Gly Val Ser Val Leu Thr Ser Lys Val
                180                 185                 190
Leu Asp Leu Lys Asn Tyr Ile Asp Lys Gln Leu Leu Pro Ile Val Asn
            195                 200                 205
Lys Gln Ser Cys Ser Ile Pro Asn Ile Glu Thr Val Ile Glu Phe Gln
        210                 215                 220
Gln Lys Asn Asn Arg Leu Leu Glu Ile Thr Arg Glu Phe Ser Val Asn
225                 230                 235                 240
Ala Gly Val Thr Thr Pro Val Ser Thr Tyr Met Leu Thr Asn Ser Glu
                245                 250                 255
Leu Leu Ser Leu Ile Asn Asp Met Pro Ile Thr Asn Asp Gln Lys Lys
                260                 265                 270
Leu Met Ser Asn Asn Val Gln Ile Val Arg Gln Gln Ser Tyr Ser Ile
            275                 280                 285
Met Ser Ile Ile Lys Glu Glu Val Leu Ala Tyr Val Val Gln Leu Pro
        290                 295                 300
Leu Tyr Gly Val Ile Asp Thr Pro Cys Trp Lys Leu His Thr Ser Pro
305                 310                 315                 320
Leu Cys Thr Thr Asn Thr Lys Glu Gly Ser Asn Ile Cys Leu Thr Arg
                325                 330                 335
Thr Asp Arg Gly Trp Tyr Cys Asp Asn Ala Gly Ser Val Ser Phe Phe
                340                 345                 350
Pro Gln Ala Glu Thr Cys Lys Val Gln Ser Asn Arg Val Phe Cys Asp
            355                 360                 365
Thr Met Asn Ser Leu Thr Leu Pro Ser Glu Val Asn Leu Cys Asn Val
        370                 375                 380
Asp Ile Phe Asn Pro Lys Tyr Asp Cys Lys Ile Met Thr Ser Lys Thr
385                 390                 395                 400
Asp Val Ser Ser Ser Val Ile Thr Ser Leu Gly Ala Ile Val Ser Cys
                405                 410                 415
Tyr Gly Lys Thr Lys Cys Thr Ala Ser Asn Lys Asn Arg Gly Ile Ile
                420                 425                 430
Lys Thr Phe Ser Asn Gly Cys Asp Tyr Val Ser Asn Lys Gly Val Asp
            435                 440                 445
Thr Val Ser Val Gly Asn Thr Leu Tyr Tyr Val Asn Lys Gln Glu Gly
        450                 455                 460
Lys Ser Leu Tyr Val Lys Gly Glu Pro Ile Ile Asn Phe Tyr Asp Pro
465                 470                 475                 480
Leu Val Phe Pro Ser Asn Glu Phe Asp Ala Ser Ile Ser Gln Val Asn
                485                 490                 495
Glu Lys Ile Asn Gln Ser Leu Ala Phe Ile Arg Lys Ser Asp Glu Leu
                500                 505                 510
Leu Ser Ala Ile Gly Gly Tyr Ile Pro Glu Ala Pro Arg Asp Gly Gln
            515                 520                 525
Ala Tyr Val Arg Lys Asp Gly Glu Trp Val Leu Leu Ser Thr Phe Leu
        530                 535                 540
```

```
<210> SEQ ID NO 4
<211> LENGTH: 12
<212> TYPE: PRT
<213> ORGANISM: Artificial Sequence
<220> FEATURE:
<223> OTHER INFORMATION: CR9501 VHCDR1

<400> SEQUENCE: 4

Gly Ala Ser Ile Asn Ser Asp Asn Tyr Tyr Trp Thr
1               5                   10

<210> SEQ ID NO 5
<211> LENGTH: 16
<212> TYPE: PRT
<213> ORGANISM: Artificial Sequence
<220> FEATURE:
<223> OTHER INFORMATION: CR9501 VHCDR2

<400> SEQUENCE: 5

His Ile Ser Tyr Thr Gly Asn Thr Tyr Tyr Thr Pro Ser Leu Lys Ser
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: CR9501 VHCDR3

<400> SEQUENCE: 6

Cys Gly Ala Tyr Val Leu Ile Ser Asn Cys Gly Trp Phe Asp Ser
1               5                   10                  15

<210> SEQ ID NO 7
<211> LENGTH: 11
<212> TYPE: PRT
<213> ORGANISM: Artificial Sequence
<220> FEATURE:
<223> OTHER INFORMATION: CR9501 VLCDR1

<400> SEQUENCE: 7

Gln Ala Ser Gln Asp Ile Ser Thr Tyr Leu Asn
1               5                   10

<210> SEQ ID NO 8
<211> LENGTH: 7
<212> TYPE: PRT
<213> ORGANISM: Artificial Sequence
<220> FEATURE:
<223> OTHER INFORMATION: CR9501VLCDR2

<400> SEQUENCE: 8

Gly Ala Ser Asn Leu Glu Thr
1               5

<210> SEQ ID NO 9
<211> LENGTH: 9
<212> TYPE: PRT
<213> ORGANISM: Artificial Sequence
<220> FEATURE:
<223> OTHER INFORMATION: CR9501 VLCDR3

<400> SEQUENCE: 9

Gln Gln Tyr Gln Tyr Leu Pro Tyr Thr
1               5
```

-continued

```
<210> SEQ ID NO 10
<211> LENGTH: 10
<212> TYPE: PRT
<213> ORGANISM: Artificial Sequence
<220> FEATURE:
<223> OTHER INFORMATION: CR9502 VHCDR1

<400> SEQUENCE: 10

Gly Phe Thr Phe Ser Gly His Thr Ile Ala
1               5                   10

<210> SEQ ID NO 11
<211> LENGTH: 17
<212> TYPE: PRT
<213> ORGANISM: Artificial Sequence
<220> FEATURE:
<223> OTHER INFORMATION: CR9502 VHCDR2

<400> SEQUENCE: 11

Trp Val Ser Thr Asn Asn Gly Asn Thr Glu Tyr Ala Gln Lys Ile Gln
1               5                   10                  15

Gly

<210> SEQ ID NO 12
<211> LENGTH: 12
<212> TYPE: PRT
<213> ORGANISM: Artificial Sequence
<220> FEATURE:
<223> OTHER INFORMATION: CR9502 VHCDR3

<400> SEQUENCE: 12

Glu Trp Leu Val Met Gly Gly Phe Ala Phe Asp His
1               5                   10

<210> SEQ ID NO 13
<211> LENGTH: 11
<212> TYPE: PRT
<213> ORGANISM: Artificial Sequence
<220> FEATURE:
<223> OTHER INFORMATION: CR9502 LVCDR1

<400> SEQUENCE: 13

Gly Ala Asn Asn Ile Gly Ser Gln Asn Val His
1               5                   10

<210> SEQ ID NO 14
<211> LENGTH: 7
<212> TYPE: PRT
<213> ORGANISM: Artificial Sequence
<220> FEATURE:
<223> OTHER INFORMATION: CR9502 VLCDR2

<400> SEQUENCE: 14

Asp Asp Arg Asp Arg Pro Ser
1               5

<210> SEQ ID NO 15
<211> LENGTH: 12
<212> TYPE: PRT
<213> ORGANISM: Artificial Sequence
<220> FEATURE:
<223> OTHER INFORMATION: CR9502 VLCDR3

<400> SEQUENCE: 15

Gln Val Trp Asp Ser Ser Arg Asp Gln Ala Val Ile
1               5                   10
```

-continued

```
<210> SEQ ID NO 16
<211> LENGTH: 228
<212> TYPE: PRT
<213> ORGANISM: Artificial Sequence
<220> FEATURE:
<223> OTHER INFORMATION: CR9501 heavy chain

<400> SEQUENCE: 16

Gln Val Gln Leu Val Gln Ser Gly Pro Gly Leu Val Lys Pro Ser Gln
1               5                   10                  15

Thr Leu Ala Leu Thr Cys Asn Val Ser Gly Ala Ser Ile Asn Ser Asp
            20                  25                  30

Asn Tyr Tyr Trp Thr Trp Ile Arg Gln Arg Pro Gly Gly Gly Leu Glu
        35                  40                  45

Trp Ile Gly His Ile Ser Tyr Thr Gly Asn Thr Tyr Tyr Thr Pro Ser
    50                  55                  60

Leu Lys Ser Arg Leu Ser Met Ser Leu Glu Thr Ser Gln Ser Gln Phe
65                  70                  75                  80

Ser Leu Arg Leu Thr Ser Val Thr Ala Ala Asp Ser Ala Val Tyr Phe
                85                  90                  95

Cys Ala Ala Cys Gly Ala Tyr Val Leu Ile Ser Asn Cys Gly Trp Phe
            100                 105                 110

Asp Ser Trp Gly Gln Gly Thr Gln Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys
225

<210> SEQ ID NO 17
<211> LENGTH: 214
<212> TYPE: PRT
<213> ORGANISM: Artificial Sequence
<220> FEATURE:
<223> OTHER INFORMATION: CR9501 Light chain

<400> SEQUENCE: 17

Glu Ile Val Met Thr Gln Ser Pro Ser Ser Leu Ser Ala Ser Ile Gly
1               5                   10                  15

Asp Arg Val Thr Ile Thr Cys Gln Ala Ser Gln Asp Ile Ser Thr Tyr
            20                  25                  30

Leu Asn Trp Tyr Gln Gln Lys Pro Gly Gln Ala Pro Arg Leu Leu Ile
        35                  40                  45

Tyr Gly Ala Ser Asn Leu Glu Thr Gly Val Pro Ser Arg Phe Thr Gly
    50                  55                  60

Ser Gly Tyr Gly Thr Asp Phe Ser Val Thr Ile Ser Ser Leu Gln Pro
65                  70                  75                  80
```

```
Glu Asp Ile Ala Thr Tyr Tyr Cys Gln Gln Tyr Gln Tyr Leu Pro Tyr
                85                  90                  95

Thr Phe Ala Pro Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 18
<211> LENGTH: 224
<212> TYPE: PRT
<213> ORGANISM: Artificial Sequence
<220> FEATURE:
<223> OTHER INFORMATION: CR9502 Heavy chain

<400> SEQUENCE: 18

Glu Val Gln Leu Leu Gln Ser Gly Ala Glu Leu Lys Lys Pro Gly Ala
1               5                   10                  15

Ser Val Lys Ile Ser Cys Lys Thr Ser Gly Phe Thr Phe Ser Gly His
                20                  25                  30

Thr Ile Ala Trp Val Arg Gln Ala Pro Gly Gln Gly Leu Glu Trp Met
            35                  40                  45

Gly Trp Val Ser Thr Asn Asn Gly Asn Thr Glu Tyr Ala Gln Lys Ile
    50                  55                  60

Gln Gly Arg Val Thr Met Thr Met Asp Thr Ser Thr Ser Thr Val Tyr
65                  70                  75                  80

Met Glu Leu Arg Ser Leu Thr Ser Asp Asp Thr Ala Val Tyr Phe Cys
                85                  90                  95

Ala Arg Glu Trp Leu Val Met Gly Gly Phe Ala Phe Asp His Trp Gly
            100                 105                 110

Gln Gly Thr Leu Leu Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220
```

<210> SEQ ID NO 19
<211> LENGTH: 215
<212> TYPE: PRT
<213> ORGANISM: Artificial Sequence
<220> FEATURE:
<223> OTHER INFORMATION: CR9502 Light chain

<400> SEQUENCE: 19

```
Gln Ser Val Leu Thr Gln Ala Ser Ser Val Ser Val Ala Pro Gly Gln
1               5                   10                  15

Thr Ala Arg Ile Thr Cys Gly Ala Asn Asn Ile Gly Ser Gln Asn Val
            20                  25                  30

His Trp Tyr Gln Gln Lys Pro Gly Gln Ala Pro Val Leu Val Val Tyr
        35                  40                  45

Asp Asp Arg Asp Arg Pro Ser Gly Ile Pro Asp Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Arg Asp Gln
                85                  90                  95

Ala Val Ile Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Ile Ala Pro Thr Glu Cys Ser
    210                 215
```

<210> SEQ ID NO 20
<211> LENGTH: 1632
<212> TYPE: DNA
<213> ORGANISM: Artificial Sequence
<220> FEATURE:
<223> OTHER INFORMATION: Nucleotide sequence encoding PRPM

<400> SEQUENCE: 20

```
atggaactgc tgatcctgaa ggccaacgcc atcaccacca tcctgaccgc cgtgaccttc      60
tgcttcgcca gcggccagaa catcaccgag gaattctacc agagcaccctg tagcgccgtg    120 tccaagggct acctgagcgc cctgagaacc ggctggtaca ccagcgtgat caccatcgag    180
ctgagcaaca tcaaggaaat caagtgcaac ggcaccgacg ccaaggtcaa gctgatcaag    240
caggaactgg acaagtacaa gaacgccgtg accgagctgc agctgctgat gcagagcacc    300
cccgccacca caaccgggc cagacgcgag ctgccccggt tcatgaacta cacccctgaac   360 aacgccaaaa agaccaacgt gaccctgagc aagaagcgga agcggcggtt cctgggcttc    420
ctgctgggcg tgggctctgc cattgctagc ggcgtggccg tgtctaaggt gctgcacctg    480
```

```
gaaggcgaag tgaacaagat caagagcgcc ctgctgagca ccaacaaggc cgtggtgtcc      540
ctgagcaacg gcgtgtccgt gctgaccagc aaggtgctgg atctgaagaa ctacatcgac      600
aagcagctgc tgcccatcgt gaacaagcag agctgcagca tccccaacat cgagacagtg      660
atcgagttcc agcagaagaa caaccggctg ctggaaatca cccgcgagtt cagcgtgaac      720
gctggcgtga ccaccccccgt gtccacctac atgctgacca cagcgagct gctgagcctg       780 atcaacgaca tgcccatcac caacgaccag aaaaagctga tgagcaacaa cgtgcagatc      840
gtgcggcagc agagctactc catcatgagc atcatcaaag aagaggtgct ggcctacgtg      900
gtgcagctgc ccctgtacgg cgtgatcgac accccctgct ggaagctgca caccagcccc      960
ctgtgcacca ccaacaccaa agagggcagc aacatctgcc tgacccggac cgaccggggc     1020
tggtactgcg ataatgccgg ctccgtgtca ttctttccac aggccgagac atgcaaggtg     1080
cagagcaacc gggtgttctg cgacaccatg aacagcctga ccctgcccctc cgaagtgaac     1140 ctgtgcaacg tggacatctt caaccctaag tacgactgca agatcatgac cagcaagacc     1200
gacgtgtcca gctccgtgat caccctccctg ggcgccatcg tgtcctgcta cggcaagacc     1260
aagtgcaccg ccagcaacaa gaaccggggc atcatcaaga ccttcagcaa cggctgcgac     1320
tacgtgtcca caaggggggt ggacaccgtg tccgtgggca cacccctgta ctacgtgaac     1380
aaacaggaag gcaagagcct gtacgtgaag ggcgagccca tcatcaactt ctacgacccc     1440
ctggtgttcc ccagcaacga gttcgacgcc agcatcagcc aggtcaacga gaagatcaac     1500
cagagcctgg ccttcatcag aaagagcgac gagctgctgt ccgccatcgg cggctacatc     1560
cccgaggccc ctagagatgg ccaggcctac gtgcggaagg acggcgagtg ggtgctgctg     1620
tctaccttcc tg                                                         1632

<210> SEQ ID NO 21
<211> LENGTH: 1632
<212> TYPE: DNA
<213> ORGANISM: Artificial Sequence
<220> FEATURE:
<223> OTHER INFORMATION: Nucleotide sequence encoding PRQM

<400> SEQUENCE: 21
atggaactgc tgatcctgaa ggccaacgcc atcaccacca tcctgaccgc cgtgaccttc       60
tgcttcgcca gcggccagaa catcaccgag gaattctacc agagcaccty tagcgccgtg      120
tccaagggct acctgagcgc cctgagaacc ggctggtaca ccagcgtgat caccatcgag      180
ctgagcaaca tcaaggaaat caagtgcaac ggcaccgacg ccaaggtcaa gctgatcaag      240
caggaactgg acaagtacaa gaacgccgtg accgagctgc agctgctgat gcagagcacc      300
cccgccacca caaccggggc cagacgcgag ctgccccggt tcatgaacta caccctgaac      360
aacgccaaaa agaccaacgt gaccctgagc aagaagcgga gcggcggtt cctgggcttc      420 ctgctgggcg tgggctctgc cattgctagc ggcgtggccg tgtctaaggt gctgcacctg      480
gaaggcgaag tgaacaagat caagagcgcc ctgctgagca ccaacaaggc cgtggtgtcc      540
ctgagcaacg gcgtgtccgt gctgaccagc aaggtgctgg atctgaagaa ctacatcgac      600
aagcagctgc tgcccatcgt gaacaagcag agctgcagca tccccaacat cgagacagtg      660
atcgagttcc agcagaagaa caaccggctg ctggaaatca cccgcgagtt cagcgtgaac      720
gctggcgtga ccaccccccgt gtccacctac atgctgacca cagcgagct gctgagcctg       780 atcaacgaca tgcccatcac caacgaccag aaaaagctga tgagcaacaa cgtgcagatc      840
gtgcggcagc agagctactc catcatgagc atcatcaaag aagaggtgct ggcctacgtg      900
```

```
gtgcagctgc ccctgtacgg cgtgatcgac acccccctgct ggaagctgca caccagcccc    960
ctgtgcacca ccaacaccaa agagggcagc aacatctgcc tgacccggac cgaccggggc   1020
tggtactgcg ataatgccgg ctccgtgtca ttctttccac aggccgagac atgcaaggtg   1080
cagagcaacc gggtgttctg cgacaccatg aacagcctga ccctgccctc cgaagtgaac   1140
ctgtgcaacg tggacatctt caaccctaag tacgactgca agatcatgac cagcaagacc   1200
gacgtgtcca gctccgtgat cacctccctg ggcgccatcg tgtcctgcta cggcaagacc   1260
aagtgcaccg ccagcaacaa gaaccggggc atcatcaaga ccttcagcaa cggctgcgac   1320
tacgtgtcca caaggggggt ggacaccgtg tccgtgggca cacccctgta ctacgtgaac   1380
aaacaggaag gcaagagcct gtacgtgaag ggcgagccca tcatcaactt ctacgacccc   1440
ctggtgttcc ccagcgacga gttcgacgcc agcatcagcc aggtcaacga gaagatcaac   1500
cagagcctgg ccttcatcag aaagagcgac gagctgctgt ccgccatcgg cggctacatc   1560
cccgaggccc ctagagatgg ccaggcctac gtgcggaagg acggcgagtg ggtgctgctg   1620
tctaccttcc tg                                                       1632

<210> SEQ ID NO 22
<211> LENGTH: 1632
<212> TYPE: DNA
<213> ORGANISM: Artificial Sequence
<220> FEATURE:
<223> OTHER INFORMATION: Nucleotide sequence encoding PRPM + S46G

<400> SEQUENCE: 22
atggaactgc tgatcctgaa ggccaacgcc atcaccacca tcctgaccgc cgtgaccttc     60
tgctttgcca gcggccagaa catcaccgag gaattctacc agagcacctg tagcgccgtg    120
tccaagggct atctgggcgc cctgagaacc ggctggtaca ccagcgtgat caccatcgag    180
ctgagcaaca tcaaagaaat caagtgcaac ggcaccgacg ccaaagtgaa gctgatcaag    240
caggaactgg acaagtacaa gaatgccgtg accgaactgc agctgctgat gcagagcacc    300
cccgccacca caaccggggc cagaagagaa ctgcccagat tcatgaacta ccccctgaac    360
aacgccaaaa agaccaacgt gaccctgagc aagaagcgga agcggcggtt cctgggcttt    420
ctgctgggag tgggaagcgc cattgctagc ggagtggccg tgtctaaggt gctgcacctg    480
gaaggcgaag tgaacaagat caagagcgcc ctgctgagca ccaacaaggc cgtggtgtct    540
ctgagcaacg gcgtgtccgt gctgaccagc aaggtgctgg atctgaagaa ctacatcgac    600
aaacagctgc tgcccatcgt gaacaagcag agctgcagca tccccaacat cgagacagtg    660
atcgagttcc agcagaagaa caaccggctg ctggaaatca cccgcgagtt cagcgtgaac    720
gctggcgtga ccacccccgt gtccacctac atgctgacca cagcgagct gctgtccctg    780 atcaacgaca tgcccatcac caacgaccag aaaaagctga tgagcaacaa cgtgcagatc    840
gtgcggcagc agagctactc catcatgagc attatcaaag aagaggtgct ggcctacgtg    900
gtgcagctgc tctctgtacgg cgtgatcgac acccccctgct ggaagctgca caccagccct    960
ctgtgcacca ccaacaccaa agagggcagc aacatctgcc tgacccggac cgacagaggc   1020
tggtactgcg ataatgccgg ctccgtctca ttctttccac aagccgagac atgcaaggtg   1080
cagagcaacc gggtgttctg cgacaccatg aacagcctga ccctgccctc cgaagtgaat   1140
ctgtgcaacg tggacatctt caaccctaag tacgactgca agatcatgac ctccaagacc   1200
gacgtgtcca gctccgtgat cacaagcctg ggcgccatcg tgtcctgcta cggcaagacc   1260
```

```
aagtgcaccg ccagcaacaa gaaccggggc atcatcaaga ccttcagcaa cggctgcgac    1320
tacgtgtcca acaagggggt ggacaccgtg tctgtgggca acaccctgta ctacgtgaac    1380
aaacaggaag gcaagagcct gtacgtgaag ggcgagccca tcatcaactt ctacgacccc    1440
ctggtgttcc ccagcaacga gttcgacgcc agcatcagcc aagtgaacga gaagatcaac    1500
cagagcctgg ccttcatcag aaagtccgat gagctgctga gcgccatcgg cggctacatc    1560
cctgaggccc ctagagatgg ccaggcctat gtgcggaagg acggcgaatg ggtgctgctg    1620 tctaccttc  tg                                                         1632
```

STABILIZED SOLUBLE PRE-FUSION RSV F PROTEINS

CROSS-REFERENCE TO RELATED APPLICATION

This application is a Section 371 of International Application No. PCT/EP2017/057962, filed Apr. 4, 2017, which was published in the English language on Oct. 12, 2017, under International Publication No. WO 2017/174568 A1 which claims priority under 35 U.S.C. § 119(b) to European Application No. 16163810.1, filed Apr. 5, 2016, the disclosures of which are incorporated herein by reference in their entirety.

REFERENCE TO SEQUENCE LISTING SUBMITTED ELECTRONICALLY

This application contains a sequence listing, which is submitted electronically via EFS-Web as an ASCII formatted sequence listing with a file name "Sequence Listing 688097 535US", creation date of Oct. 3, 2018, and having a size of about 31.8 KB. The sequence listing submitted via EFS-Web is part of the specification and is herein incorporated by reference in its entirety.

The present invention relates to the field of medicine. The invention in particular relates to recombinant pre-fusion RSV F proteins and uses thereof; e.g. as a vaccine.

BACKGROUND OF THE INVENTION

Respiratory syncytial virus (RSV) is a highly contagious childhood pathogen of the respiratory tract which is believed to be responsible for 200,000 childhood deaths annually. In children younger than 2 years, RSV accounts for approximately 50% of the hospitalizations due to respiratory infections, with a peak of hospitalization occurring at 2-4 months of age. It has been reported that almost all children will have experienced infection with RSV by the age of two, and repeated infection during life is attributed to low natural immunity. In the elderly, the RSV disease burden is similar to those caused by non-pandemic influenza A infections.

To infect a host cell, RSV, like other enveloped viruses such as influenza virus and HIV, require fusion of the viral membrane with a host cell membrane. For RSV the conserved fusion protein (RSV F protein) fuses the viral and host cell cellular membranes. In current models, based on paramyxovirus studies, the RSV F protein initially folds into a "pre-fusion" conformation. The metastable structure has recently been solved in complex with a stabilizing neutralizing antibody Fab fragment (McLellan et al., Science 340(6136):1113-7, 2013). During cell entry, the pre-fusion conformation undergoes refolding and conformational changes to its "post-fusion" conformation (McLellan, J. Virol 85(15):7788-96, 2010; Swanson, PNAS 108(23): 9619-24, 2011). Thus, the RSV F protein is a metastable protein that drives membrane fusion by coupling irreversible protein refolding to membrane juxtaposition by initially folding into a metastable form (pre-fusion conformation) that subsequently undergoes discrete/stepwise conformational changes to a lower energy conformation (post-fusion conformation). These observations suggest that pre-fusion and post-fusion RSV F protein are antigenically distinct (Calder, L. J. et al. Virology 271, 122-131 (2000)). It is clear from electron microscopy of RSV-F that large structural differences between the pre-fusion and post-fusion F trimer exist, which has recently been confirmed by crystallography (McLellan J. S. et al. Science 340(6136):1113-7 (2013) and McLellan J. S. et al. Science 342(6158): 592-8 (2013)) and it was shown that most of the neutralizing antibodies in the serum of RSV-positive individuals are binding to pre-fusion F (Ngwuta et. al., Science Translational Medicine, 7(309): 309ra162, 1-9).

A vaccine against RSV infection is not currently available, but is desired. Vaccine candidates based on the RSV F protein have failed due to problems with e.g. stability, purity, reproducibility, and potency. As indicated above, crystal structures have revealed a large conformational change between the pre-fusion and post-fusion states. The magnitude of the rearrangement suggested that only a portion of antibodies directed to the post-fusion conformation of RSV-F will be able to cross react with the native conformation of the pre-fusion spike on the surface of the virus. Accordingly, efforts to produce a vaccine against RSV have focused on developing vaccines that contain pre-fusion forms of RSV F protein (see, e.g., WO20101149745, WO2010/1149743, WO2009/1079796, WO2012/158613). However, these efforts have not yet yielded stable pre-fusion RSV F proteins that could be used as candidates for testing in humans.

Therefore, a need remains for efficient vaccines and methods of vaccinating against RSV, in particular comprising RSV F proteins in the pre-fusion conformation. The present invention aims at providing such vaccines and methods for vaccinating against RSV in a safe and efficacious manner.

SUMMARY OF THE INVENTION

The present invention provides stable, recombinant, pre-fusion respiratory syncytial virus (RSV) fusion (F) proteins, i.e. recombinant RSV F proteins in soluble form (i.e. not membrane bound) that are stabilized in the pre-fusion conformation, wherein the RSV F protein comprises an amino acid sequence selected from the group consisting of SEQ ID NO: 1, SEQ ID NO: 2 and SEQ ID NO: 3, or fragments thereof.

In certain embodiments, the RSV F proteins, or fragments thereof, comprise at least one epitope that is specific to the pre-fusion conformation F protein, wherein the at least one epitope is recognized by a pre-fusion specific monoclonal antibody comprising a heavy chain CDR1 region of SEQ ID NO: 4, a heavy chain CDR2 region of SEQ ID NO: 5, a heavy chain CDR3 region of SEQ ID NO: 6 and a light chain CDR1 region of SEQ ID NO: 7, a light chain CDR2 region of SEQ ID NO: 8, and a light chain CDR3 region of SEQ ID NO: 9, and/or a pre-fusion specific monoclonal antibody, comprising a heavy chain CDR1 region of SEQ ID NO: 10, a heavy chain CDR2 region of SEQ ID NO: 11, a heavy chain CDR3 region of SEQ ID NO: 12 and a light chain CDR1 region of SEQ ID NO: 13, a light chain CDR2 region of SEQ ID NO: 14, and a light chain CDR3 region of SEQ ID NO: 15.

In certain embodiments, the RSV F proteins are trimeric.

The invention also provides nucleic acid molecules encoding the pre-fusion RSV F proteins or fragments thereof according to the invention and vectors comprising such nucleic acid molecules.

The invention also relates to compositions, preferably immunogenic compositions, comprising said RSV pre-fusion F protein (or fragments thereof), nucleic acid molecule encoding said RSV pre-fusion F protein, and to the use thereof in inducing an immune response against RSV F protein, in particular to the use thereof as a vaccine. The invention also relates to methods for inducing an anti-respiratory syncytial virus (RSV) immune response in a subject, comprising administering to the subject an effective amount of a pre-fusion RSV F protein, a nucleic acid molecule encoding said RSV F protein, and/or a vector comprising said nucleic acid molecule. Preferably, the induced immune response is characterized by neutralizing antibodies to RSV and/or protective immunity against RSV. In particular aspects, the invention relates to a method for inducing neutralizing anti-respiratory syncytial virus (RSV) F protein antibodies in a subject, comprising administering to the subject an effective amount of an immunogenic composition comprising a pre-fusion RSV F protein, a nucleic acid molecule encoding said RSV F protein, and/or a vector comprising said nucleic acid molecule.

DETAILED DESCRIPTION OF THE INVENTION

Figure 1:
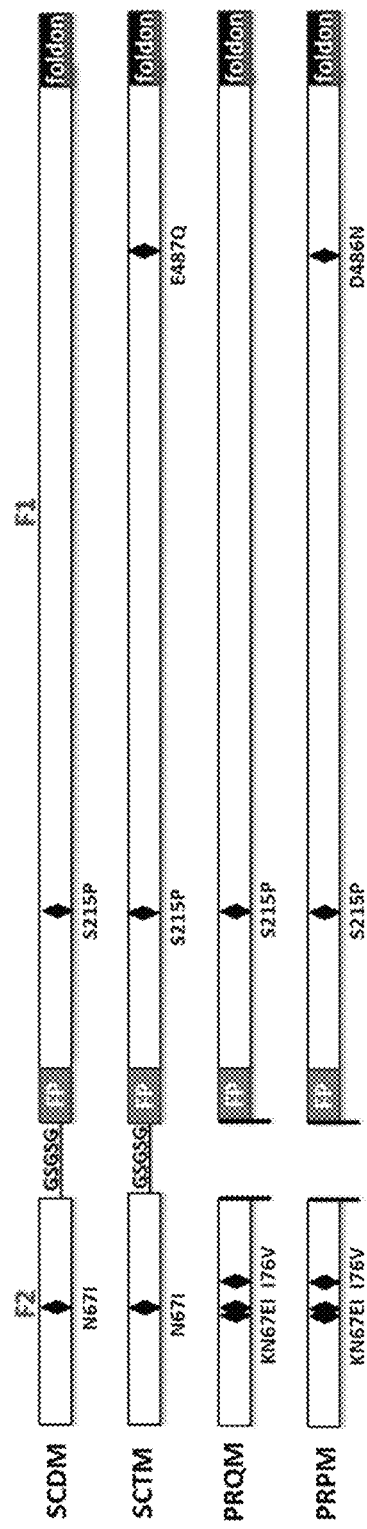
FIG. 1. Schematic representation of RSV F variants. SCDM—single-chain double mutant, SCTM—single-chain triple mutant, PRQM—processed quadruple mutant and PRPM—processed penta-mutant. Secreted proteins are presented without signal peptide and p27 fragment. F1 and F2 domains are indicated, as well as fusion peptide (FP), fibritin trimerization domain (foldon) and the linker in single-chain proteins between F2 and F1 (GSGSG). Three stabilizing mutations (N67I, S215P and D386N) (black diamonds). Two mutations to improve antigenic match to circulating strains (K66E and I76V) (grey diamonds). The residue position is numbered as in the full length wild type protein including signal peptide.

The fusion protein (F) of the respiratory syncictial virus (RSV) is involved in fusion of the viral membrane with a host cell membrane, which is required for infection. The RSV F mRNA is translated into a 574 amino acid precursor protein designated F0, which contains a signal peptide sequence of 26 amino acids at the N-terminus that is removed by a signal peptidase in the endoplasmic reticulum. F0 is cleaved at two sites (between amino acid residues 109/110 and 136/137) by cellular furin-like proteases in the trans-Golgi, removing a short glycosylated intervening sequence (also referred to a p27 region, comprising the amino acid residues 110 to 136, and generating two domains or subunits designated F1 and F2. The F1 domain (amino acid residues 137-574) contains a hydrophobic fusion peptide at its N-terminus and the C-terminus contains the transmembrane (TM) (amino acid residues 530-550) and cytoplasmic region (amino acid residues 551-574). The F2 domain (amino acid residues 27-109) is covalently linked to F1 by two disulfide bridges. The F1-F2 heterodimers are assembled as homotrimers in the virion.

A vaccine against RSV infection is not currently available, but is desired. One potential approach to producing a vaccine is a subunit vaccine based on purified RSV F protein. However, for this approach it is desirable that the purified RSV F protein is in a conformation which resembles the conformation of the pre-fusion state of RSV F protein, and which is stable over time, and can be produced in sufficient quantities. In addition, for a subunit-based vaccine, the RSV F protein needs to be truncated by deletion of the transmembrane (TM) and the cytoplasmic region to create a soluble secreted F protein (sF). Because the TM region is responsible for membrane anchoring and trimerization, the anchorless soluble F protein is considerably more labile than the full-length protein and will readily refold into the post-fusion end-state. In order to obtain soluble F protein in the stable pre-fusion conformation that shows high expression levels and high stability, the pre-fusion conformation thus needs to be stabilized.

Several mutations stabilizing RSV F protein in the pre-fusion conformation have previously been described in WO2014/174018 and WO2014/202570. The RSV F proteins according to the present invention comprise a unique and specific subset of mutations described earlier in combination with two further mutations. According to the invention it has been shown that this unique combination of mutations of the present invention results in increased RSV F protein expression levels and stability of the pre-fusion conformation.

The present invention thus provides novel stable soluble pre-fusion RSV F proteins, i.e. soluble RSV F proteins that are stabilized in the pre-fusion conformation, or fragments thereof. The RSV F proteins according to the present invention comprise an amino acid sequence selected from the group consisting of SEQ ID NO: 1, SEQ ID NO: 2 and SEQ ID NO: 3.

In the research that led to the present invention, a unique combination of mutations was introduced together with a heterologous trimerization domain in order to obtain said stable soluble pre-fusion RSV F proteins. The stable pre-fusion RSV F proteins of the invention are in the pre-fusion conformation, i.e. they comprise (display) at least one epitope that is specific to the pre-fusion conformation F protein. An epitope that is specific to the pre-fusion conformation F protein is an epitope that is not presented in the post-fusion conformation. Without wishing to be bound by any particular theory, it is believed that the pre-fusion conformation of RSV F protein may contain epitopes that are the same as those on the RSV F protein expressed on natural RSV virions, and therefore may provide advantages for eliciting protective neutralizing antibodies.

In certain embodiments, the RSV pre-fusion F proteins (or fragments thereof) of the invention comprise at least one epitope that is recognized by a pre-fusion specific monoclonal antibody, comprising a heavy chain CDR1 region of SEQ ID NO: 4, a heavy chain CDR2 region of SEQ ID NO: 5, a heavy chain CDR3 region of SEQ ID NO: 6 and a light chain CDR1 region of SEQ ID NO: 7, a light chain CDR2 region of SEQ ID NO: 8, and a light chain CDR3 region of SEQ ID NO: 9 (hereafter referred to as CR9501) and/or a pre-fusion specific monoclonal antibody, comprising a heavy chain CDR I region of SEQ ID NO: 10, a heavy chain CDR2 region of SEQ ID NO: 11, a heavy chain CDR3 region of SEQ ID NO: 12 and a light chain CDR1 region of SEQ ID NO: 13, a light chain CDR2 region of SEQ ID NO: 14, and a light chain CDR3 region of SEQ ID NO: 15 (referred to as CR9502). CR9501 and CR9502 comprise the heavy and light chain variable regions, and thus the binding specificities, of the antibodies 58C5 and 30D8, respectively, which have previously been shown to bind specifically to RSV F protein in its pre-fusion conformation and not to the post-fusion conformation (as disclosed in WO2012/006596).

In certain embodiments, the recombinant pre-fusion RSV F proteins are trimeric.

As used throughout the present application nucleotide sequences are provided from 5' to 3' direction, and amino acid sequences from N-terminus to C-terminus, as custom in the art.

As indicated above, fragments of the pre-fusion RSV F protein are also encompassed by the present invention. The fragment may result from either or both of amino-terminal (e.g. by cleaving off the signal sequence) and carboxy-terminal deletions. The fragment may be chosen to comprise an immunologically active fragment of the F protein, i.e. a part that will give rise to an immune response in a subject. This can be easily determined using in silico, in vitro and/or in vivo methods, all routine to the skilled person.

In certain embodiments, the encoded proteins according to the invention comprise a signal sequence, also referred to as leader sequence or signal peptide, corresponding to amino acids 1-26 of SEQ ID NO: 1, SEQ ID NO: 2 or SEQ ID NO: 3. Signal sequences typically are short (e.g. 5-30 amino acids long) amino acid sequences present at the N-terminus of the majority of newly synthesized proteins that are destined towards the secretory pathway, and are typically cleaved by signal peptidase to generate a free signal peptide and a mature protein.

In certain embodiments, the proteins according to the invention do not comprise a signal sequence.

The present invention further provides nucleic acid molecules encoding the RSV pre-fusion F proteins, or fragments thereof, according to the invention.

In preferred embodiments, the nucleic acid molecules encoding the RSV F proteins according to the invention are codon-optimized for expression in mammalian cells, preferably human cells. Methods of codon-optimization are known and have been described previously (e.g. WO 96/09378). A sequence is considered codon-optimized if at least one non-preferred codon as compared to a wild type sequence is replaced by a codon that is more preferred. Herein, a non-preferred codon is a codon that is used less frequently in an organism than another codon coding for the same amino acid, and a codon that is more preferred is a codon that is used more frequently in an organism than a non-preferred codon. The frequency of codon usage for a specific organism can be found in codon frequency tables, such as in http://www.kazusa.or.jp/codon. Preferably more than one non-preferred codon, preferably most or all non-preferred codons, are replaced by codons that are more preferred. Preferably the most frequently used codons in an organism are used in a codon-optimized sequence. Replacement by preferred codons generally leads to higher expression.

It will be understood by a skilled person that numerous different polynucleotides and nucleic acid molecules can encode the same protein as a result of the degeneracy of the genetic code. It is also understood that skilled persons may, using routine techniques, make nucleotide substitutions that do not affect the protein sequence encoded by the nucleic acid molecules to reflect the codon usage of any particular host organism in which the proteins are to be expressed. Therefore, unless otherwise specified, a "nucleotide sequence encoding an amino acid sequence" includes all nucleotide sequences that are degenerate versions of each other and that encode the same amino acid sequence. Nucleotide sequences that encode proteins and RNA may or may not include introns.

Nucleic acid sequences can be cloned using routine molecular biology techniques, or generated de novo by DNA synthesis, which can be performed using routine procedures by service companies having business in the field of DNA synthesis and/or molecular cloning (e.g. GeneArt, GenScripts, Invitrogen, Eurofins).

In certain embodiments, the nucleic acid molecules comprise a nucleotide sequence of SEQ ID NO. 2221, or 22.

The invention also provides vectors comprising a nucleic acid molecule as described above. In certain embodiments, a nucleic acid molecule according to the invention thus is part of a vector. Such vectors can easily be manipulated by methods well known to the person skilled in the art, and can for instance be designed for being capable of replication in prokaryotic and/or eukaryotic cells. In addition, many vectors can be used for transformation of eukaryotic cells and will integrate in whole or in part into the genome of such cells, resulting in stable host cells comprising the desired nucleic acid in their genome. The vector used can be any vector that is suitable for cloning DNA and that can be used for transcription of a nucleic acid of interest. The person skilled in the art is capable of choosing suitable expression vectors, and inserting the nucleic acid sequences of the invention in a functional manner.

Host cells comprising the nucleic acid molecules encoding the pre-fusion RSV F proteins form also part of the invention. The pre-fusion RSV F proteins may be produced through recombinant DNA technology involving expression of the molecules in host cells, e.g. Chinese hamster ovary (CHO) cells, tumor cell lines, BHK cells, human cell lines such as HEK293 cells, PER.C6 cells, or yeast, fungi, insect cells, and the like, or transgenic animals or plants. In certain embodiments, the cells are from a multicellular organism, in certain embodiments they are of vertebrate or invertebrate origin. In certain embodiments, the cells are mammalian cells. In certain embodiments, the cells are human cells. In general, the production of a recombinant proteins, such the pre-fusion RSV F proteins of the invention, in a host cell comprises the introduction of a heterologous nucleic acid molecule encoding the protein in expressible format into the host cell, culturing the cells under conditions conducive to expression of the nucleic acid molecule and allowing expression of the protein in said cell. The nucleic acid molecule encoding a protein in expressible format may be in the form of an expression cassette, and usually requires sequences capable of bringing about expression of the nucleic acid, such as enhancer(s), promoter, polyadenylation signal, and the like. The person skilled in the art is aware that various promoters can be used to obtain expression of a gene in host cells. Promoters can be constitutive or regulated, and can be obtained from various sources, including viruses, prokaryotic, or eukaryotic sources, or artificially designed.

Cell culture media are available from various vendors, and a suitable medium can be routinely chosen for a host cell to express the protein of interest, here the pre-fusion RSV F proteins. The suitable medium may or may not contain serum.

A "heterologous nucleic acid molecule" (also referred to herein as 'transgene') is a nucleic acid molecule that is not naturally present in the host cell. It is introduced into for instance a vector by standard molecular biology techniques. A transgene is generally operably linked to expression control sequences. This can for instance be done by placing the nucleic acid encoding the transgene(s) under the control of a promoter. Further regulatory sequences may be added. Many promoters can be used for expression of a transgene(s), and are known to the skilled person, e.g. these may comprise viral, mammalian, synthetic promoters, and the like. A non-limiting example of a suitable promoter for obtaining expression in eukaryotic cells is a CMV-promoter (U.S. Pat. No. 5,385,839), e.g. the CMV immediate early promoter, for instance comprising nt. −735 to +95 from the CMV immediate early gene enhancer/promoter. A polyadenylation signal, for example the bovine growth hormone polyA signal (U.S. Pat. No. 5,122,458), may be present behind the transgene(s). Alternatively, several widely used expression vectors are available in the art and from commercial sources, e.g. the pcDNA and pEF vector series of Invitrogen, pMSCV and pTK-Hyg from BD Sciences, pCMV-Script from Stratagene, etc, which can be used to recombinantly express the protein of interest, or to obtain suitable promoters and/or transcription terminator sequences, polyA sequences, and the like.

The cell culture can be any type of cell culture, including adherent cell culture, e.g. cells attached to the surface of a culture vessel or to microcarriers, as well as suspension culture. Most large-scale suspension cultures are operated as batch or fed-batch processes because they are the most straightforward to operate and scale up. Nowadays, continuous processes based on perfusion principles are becoming more common and are also suitable. Suitable culture media are also well known to the skilled person and can generally be obtained from commercial sources in large quantities, or custom-made according to standard protocols. Culturing can be done for instance in dishes, roller bottles or in bioreactors, using batch, fed-batch, continuous systems and the like. Suitable conditions for culturing cells are known (see e.g. Tissue Culture, Academic Press, Kruse and Paterson, editors (1973), and R. I. Freshney, Culture of animal cells: A manual of basic technique, fourth edition (Wiley-Liss Inc., 2000, ISBN 0-471-34889-9)).

The invention further provides compositions comprising a pre-fusion RSV F protein and/or a nucleic acid molecule, and/or a vector, as described above. The invention thus provides compositions comprising a pre-fusion RSV F protein that displays an epitope that is present in a pre-fusion conformation of the RSV F protein but is absent in the post-fusion conformation, or a fragment thereof. The invention also provides compositions comprising a nucleic acid molecule and/or a vector, encoding such pre-fusion RSV F protein or fragment thereof. The compositions preferably are immunogenic compositions comprising a pre-fusion RSV F protein, and/or a nucleic acid molecule, and/or a vector, as described above. The invention also provides the use of a stabilized pre-fusion RSV F protein or a nucleic acid molecule encoding said RSV F protein according to the invention, for inducing an immune response against RSV F protein in a subject. Further provided are methods for inducing an immune response against RSV F protein in a subject, comprising administering to the subject a pre-fusion RSV F protein, and/or a nucleic acid molecule, and/or a vector, according to the invention. Also provided are pre-fusion RSV F proteins, nucleic acid molecules, and/or vectors, according to the invention for use in inducing an immune response against RSV F protein in a subject. Further provided is the use of the pre-fusion RSV F proteins, and/or nucleic acid molecules, and/or vectors according to the invention for the manufacture of a medicament for use in inducing an immune response against RSV F protein in a subject.

The pre-fusion RSV F proteins, nucleic acid molecules, or vectors of the invention may be used for prevention (prophylaxis) and/or treatment of RSV infections. In certain embodiments, the prevention and/or treatment may be targeted at patient groups that are susceptible RSV infection. Such patient groups include, but are not limited to e.g., the elderly (e.g. ≥50 years old, ≥60 years old, and preferably ≥65 years old), the young (e.g. ≤5 years old, ≤1 year old), hospitalized patients and patients who have been treated with an antiviral compound but have shown an inadequate antiviral response.

The pre-fusion RSV F proteins, nucleic acid molecules and/or vectors according to the invention may be used e.g. in stand-alone treatment and/or prophylaxis of a disease or condition caused by RSV, or in combination with other prophylactic and/or therapeutic treatments, such as (existing or future) vaccines, antiviral agents and/or monoclonal antibodies.

The invention further provides methods for preventing and/or treating RSV infection in a subject utilizing the pre-fusion RSV F proteins, nucleic acid molecules and/or vectors according to the invention. In a specific embodiment, a method for preventing and/or treating RSV infection in a subject comprises administering to a subject in need thereof an effective amount of a pre-fusion RSV F protein, nucleic acid molecule and/or a vector, as described above. A therapeutically effective amount refers to an amount of a protein, nucleic acid molecule or vector, which is effective for preventing, ameliorating and/or treating a disease or condition resulting from infection by RSV. Prevention encompasses inhibiting or reducing the spread of RSV or inhibiting or reducing the onset, development or progression of one or more of the symptoms associated with infection by RSV. Amelioration as used in herein may refer to the reduction of visible or perceptible disease symptoms, viremia, or any other measurable manifestation of influenza infection.

For administering to subjects, such as humans, the invention may employ pharmaceutical compositions comprising a pre-fusion RSV F protein, a nucleic acid molecule and/or a vector as described herein, and a pharmaceutically acceptable carrier or excipient. In the present context, the term "pharmaceutically acceptable" means that the carrier or excipient, at the dosages and concentrations employed, will not cause any unwanted or harmful effects in the subjects to which they are administered. Such pharmaceutically acceptable carriers and excipients are well known in the art (see Remington's Pharmaceutical Sciences, 18th edition, A. R. Gennaro, Ed., Mack Publishing Company [1990]; Pharmaceutical Formulation Development of Peptides and Proteins, S. Frokjaer and L. Hovgaard, Eds., Taylor & Francis [2000]; and Handbook of Pharmaceutical Excipients, 3rd edition, A. Kibbe, Ed., Pharmaceutical Press [2000]). The RSV F proteins, or nucleic acid molecules, preferably are formulated and administered as a sterile solution although it may also be possible to utilize lyophilized preparations. Sterile solutions are prepared by sterile filtration or by other methods known per se in the art. The solutions are then lyophilized or filled into pharmaceutical dosage containers. The pH of the solution generally is in the range of pH 3.0 to 9.5, e.g. pH 5.0 to 7.5. The RSV F proteins typically are in a solution having a suitable pharmaceutically acceptable buffer, and the composition may also contain a salt. Optionally stabilizing agent may be present, such as albumin. In certain embodiments, detergent is added. In certain embodiments, the RSV F proteins may be formulated into an injectable preparation.

In certain embodiments, a composition according to the invention further comprises one or more adjuvants. Adjuvants are known in the art to further increase the immune response to an applied antigenic determinant. The terms "adjuvant" and "immune stimulant" are used interchangeably herein, and are defined as one or more substances that cause stimulation of the immune system. In this context, an adjuvant is used to enhance an immune response to the RSV F proteins of the invention. Examples of suitable adjuvants include aluminium salts such as aluminium hydroxide and/or aluminium phosphate; oil-emulsion compositions (or oil-in-water compositions), including squalene-water emulsions, such as MF59 (see e.g. WO 90/14837); saponin formulations, such as for example QS21 and Immunostimulating Complexes (ISCOMS) (see e.g. U.S. Pat. No. 5,057, 540; WO 90/03184, WO 96/11711, WO 2004/004762, WO 2005/002620); bacterial or microbial derivatives, examples of which are monophosphoryl lipid A (MPL), 3-O-deacylated MPL (3dMPL), CpG-motif containing oligonucleotides, ADP-ribosylating bacterial toxins or mutants thereof, such as *E. coli* heat labile enterotoxin LT, cholera toxin CT, and the like; eukaryotic proteins (e.g. antibodies or fragments thereof (e.g. directed against the antigen itself or CD1a, CD3, CD7, CD80) and ligands to receptors (e.g. CD40L, GMCSF, GCSF, etc), which stimulate immune response upon interaction with recipient cells. In certain embodiments the compositions of the invention comprise aluminium as an adjuvant, e.g. in the form of aluminium hydroxide, aluminium phosphate, aluminium potassium phosphate, or combinations thereof, in concentrations of 0.05-5 mg, e.g. from 0.075-1.0 mg, of aluminium content per dose.

The pre-fusion RSV F proteins may also be administered in combination with or conjugated to nanoparticles, such as e.g. polymers, liposomes, virosomes, virus-like particles or self-assembling protein particles. The pre-fusion F proteins may be combined with, encapsidated in or conjugated to the nanoparticles with or without adjuvant. Encapsulation within liposomes is described, e.g. in U.S. Pat. No. 4,235, 877. Conjugation to macromolecules is disclosed, for example in U.S. Pat. No. 4,372,945 or 4,474,757.

In other embodiments, the compositions do not comprise adjuvants.

In certain embodiments, the invention provides methods for making a vaccine against respiratory syncytial virus (RSV), comprising providing a composition according to the invention and formulating it into a pharmaceutically acceptable composition. The term "vaccine" refers to an agent or composition containing an active component effective to induce a certain degree of immunity in a subject against a certain pathogen or disease, which will result in at least a decrease (up to complete absence) of the severity, duration or other manifestation of symptoms associated with infection by the pathogen or the disease. In the present invention, the vaccine comprises an effective amount of a pre-fusion RSV F protein and/or a nucleic acid molecule encoding a pre-fusion RSV F protein, and/or a vector comprising said nucleic acid molecule, which results in an immune response against the F protein of RSV. This provides a method of preventing serious lower respiratory tract disease leading to hospitalization and the decrease in frequency of complications such as pneumonia and bronchiolitis due to RSV infection and replication in a subject. The term "vaccine"

according to the invention implies that it is a pharmaceutical composition, and thus typically includes a pharmaceutically acceptable diluent, carrier or excipient. It may or may not comprise further active ingredients. In certain embodiments it may be a combination vaccine that further comprises other components that induce an immune response, e.g. against other proteins of RSV and/or against other infectious agents. The administration of further active components may for instance be done by separate administration or by administering combination products of the vaccines of the invention and the further active components.

Compositions may be administered to a subject, e.g. a human subject. The total dose of the RSV F proteins in a composition for a single administration can for instance be about 0.01 μg to about 10 mg, e.g. 1 μg-1 mg, e.g. 10 μg-100 μg. Determining the recommended dose will be carried out by experimentation and is routine for those skilled in the art.

Administration of the compositions according to the invention can be performed using standard routes of administration. Non-limiting embodiments include parenteral administration, such as intradermal, intramuscular, subcutaneous, transcutaneous, or mucosal administration, e.g. intranasal, oral, and the like. In one embodiment a composition is administered by intramuscular injection. The skilled person knows the various possibilities to administer a composition, e.g. a vaccine in order to induce an immune response to the antigen(s) in the vaccine.

A subject as used herein preferably is a mammal, for instance a rodent, e.g. a mouse, a cotton rat, or a non-human-primate, or a human. Preferably, the subject is a human subject.

The proteins, nucleic acid molecules, vectors, and/or compositions may also be administered, either as prime, or as boost, in a homologous or heterologous prime-boost regimen. If a boosting vaccination is performed, typically, such a boosting vaccination will be administered to the same subject at a time between one week and one year, preferably between two weeks and four months, after administering the composition to the subject for the first time (which is in such cases referred to as 'priming vaccination'). In certain embodiments, the administration comprises a prime and at least one booster administration.

In addition, the proteins of the invention may be used as diagnostic tool, for example to test the immune status of an individual by establishing whether there are antibodies in the serum of such individual capable of binding to the protein of the invention. The invention thus also relates to an in vitro diagnostic method for detecting the presence of an RSV infection in a patient said method comprising the steps of a) contacting a biological sample obtained from said patient with a protein according to the invention; and b) detecting the presence of antibody-protein complexes.

EXAMPLES

Example 1: Generation of the Stable Pre Fusion RSV F Protein

Several pre-fusion RSV F protein variants were produced, which are schematically represented in FIG. 1. All candidates comprise a fibritin trimerization domain (foldon) (GYIPEAPRDGQAYVRKDGEWVLLSTFL; SEQ ID NO: 20), linked to the amino acid residue 495 of the RSV A2 F1 domain.

Figure 2:
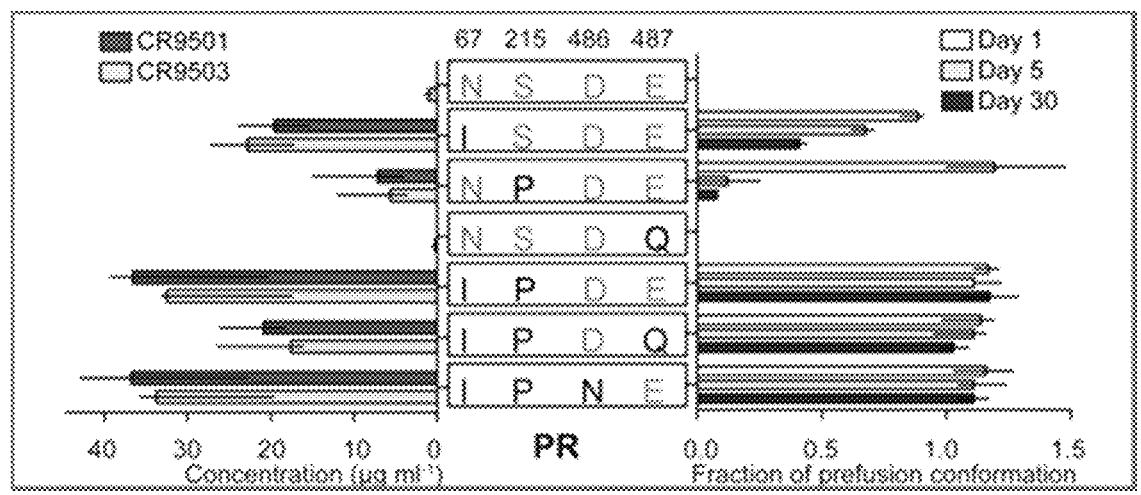
FIG. 2. Protein expression levels and pre-fusion stability of processed RSV F PR-A2 variants with multiple amino acid substitutions. Protein expression levels in cell culture supernatants were tested 72 hours post transfection by quantitative octet (Q-Octet) with CR9501 and CR9503 (bars to the left) and fraction of RSV F protein binding to pre-fusion specific CR9501 antibody on the day of harvest and after storage at 4° C. for indicated period of time (bars to the right). Bars represent average of 2-4 measurements, lines represent range of values.
Figure 3:
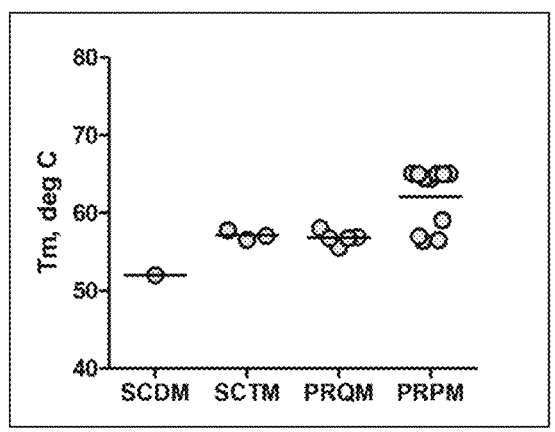
FIG. 3. Melting temperatures (Tm) of the purified RSV-F proteins. Each measurement is represented by a dot.

In the processed versions of RSV F (i.e. the versions which are cleaved removing the p27 region) the N67I substitution had the strongest effect on both the expression level and stability but fully stable pre-fusion F protein was obtained only when the 67 and 215 substitutions were combined, resulting in a 20-fold expression level increase (FIG. 2). Addition of a third amino acid substitution did not improve expression level or stability as measured by storage stability at 4° C. However, when the RSV F proteins were purified and further characterized, it turned out that the extra third substitution significantly stabilizes the pre-fusion F protein as measured by the more stringent temperature stability test (by Differential Scanning Fluorimetry assay—DSF) (FIG. 3).

Figure 4:
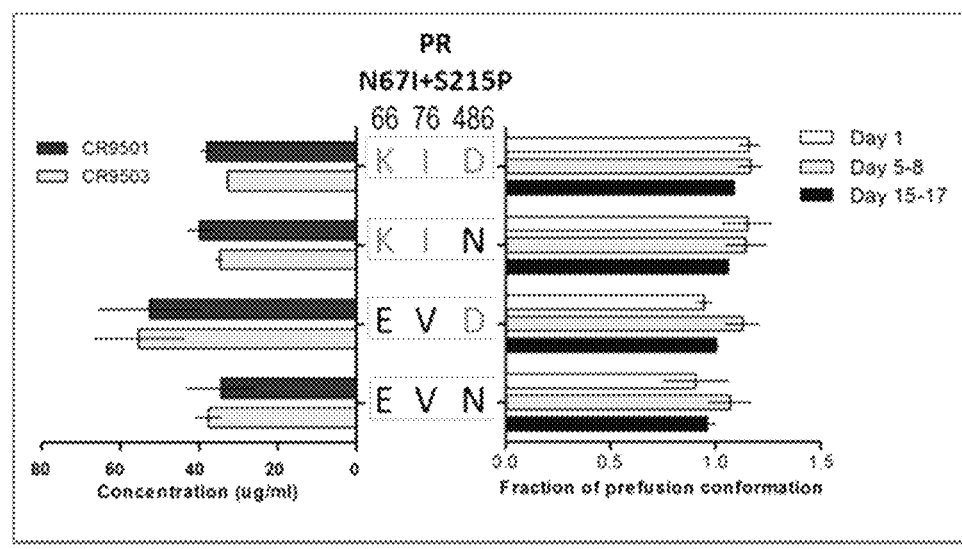
FIG. 4. K66E and I76V amino acid substitutions did not have effect on F protein expression levels and pre-fusion stability. Protein expression levels in cell culture supernatants were tested 96 hours post transfection by Q-Octet with CR9501 and CR9503 (bars to the left) and fraction of RSV F protein binding to pre-fusion specific CR9501 antibody on the day of harvest and after storage at 4° C. for indicated period of time (bars to the right). Bars represent average of 2 measurements, lines represent range of values.

Because the A2 strain that was used as a parental sequence for the RSV F protein variants described previously (WO2014/174018 and WO2014/202570) is a cell line adapted laboratory strain which had accumulated two unique and rare mutations in the apex K66 and I76), it was decided to mutate these two residues to match the natural clinical isolates (K66E, I76V). The K66E and I76V mutations were included in the new processed protein design to make the sequence closer to the natural virus isolates. The K66E+I76V substitutions were tested in selected stabilized variants to demonstrate that the amino acid substitutions did not have negative effect on protein expression or stability. It was shown that the proteins were stable in cell culture supernatants for longer than 2 weeks. There was no negative effect on the expression level of the F proteins, on the contrary, RSV F protein with N67I, S215P, K66E and I76V mutations expressed to a higher level than protein with only N67I and S215P (FIG. 4).

The processed RSV F proteins with N67I, S215P, K66E and I76V (named PRQM for processed quadruple-mutant) and with N67I, S215P, K66E, I76V and D486N (named PRPM for processed penta-mutant) were purified and further characterized.

The screening of the stabilizing mutations for the RSV F protein was performed in suspension HEK cells (FreeStyle 293F). These cells are convenient to use in a research laboratory because they are adapted to simple transfection protocol and express proteins at a high level. For big scale and GMP protein production CHO cells are often the cell line of choice. Therefore expression and stability of several preferred F protein designs was tested in suspension CHO cells (FreeStyle CHO-S). CHO-S cells are difficult to transfect and therefore overall expression levels were expected to be lower than in HEK cells. During analysis therefore we focused on relative expression of the proteins and their stability.

Figure 5:
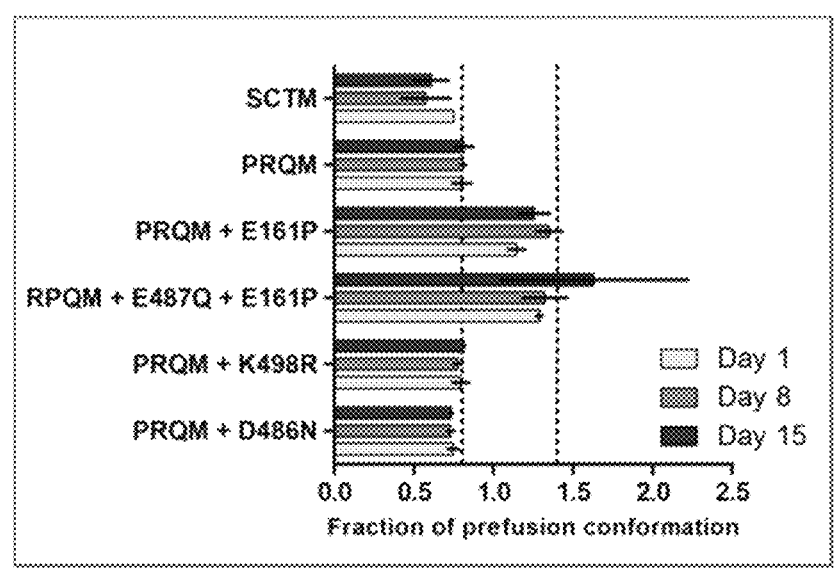
FIG. 5: Pre-fusion stability of the F protein variants in CHO cell culture supernatant. Protein expression levels in cell culture supernatants were tested 96 hours post transfection by Q-Octet with CR9501 and CR9503 and fraction of RSV F protein binding to pre-fusion specific CR9501 antibody on the day of harvest and after storage at 4° C. for indicated period of time. Bars represent average of 2 measurements, lines represent range of values. PRQM—PR-A2 with N67I, S215P, K66E, and I76V; PRPM—PR-A2 with N67I, S215P, K66E, I76V and D486N.
Figure 6:
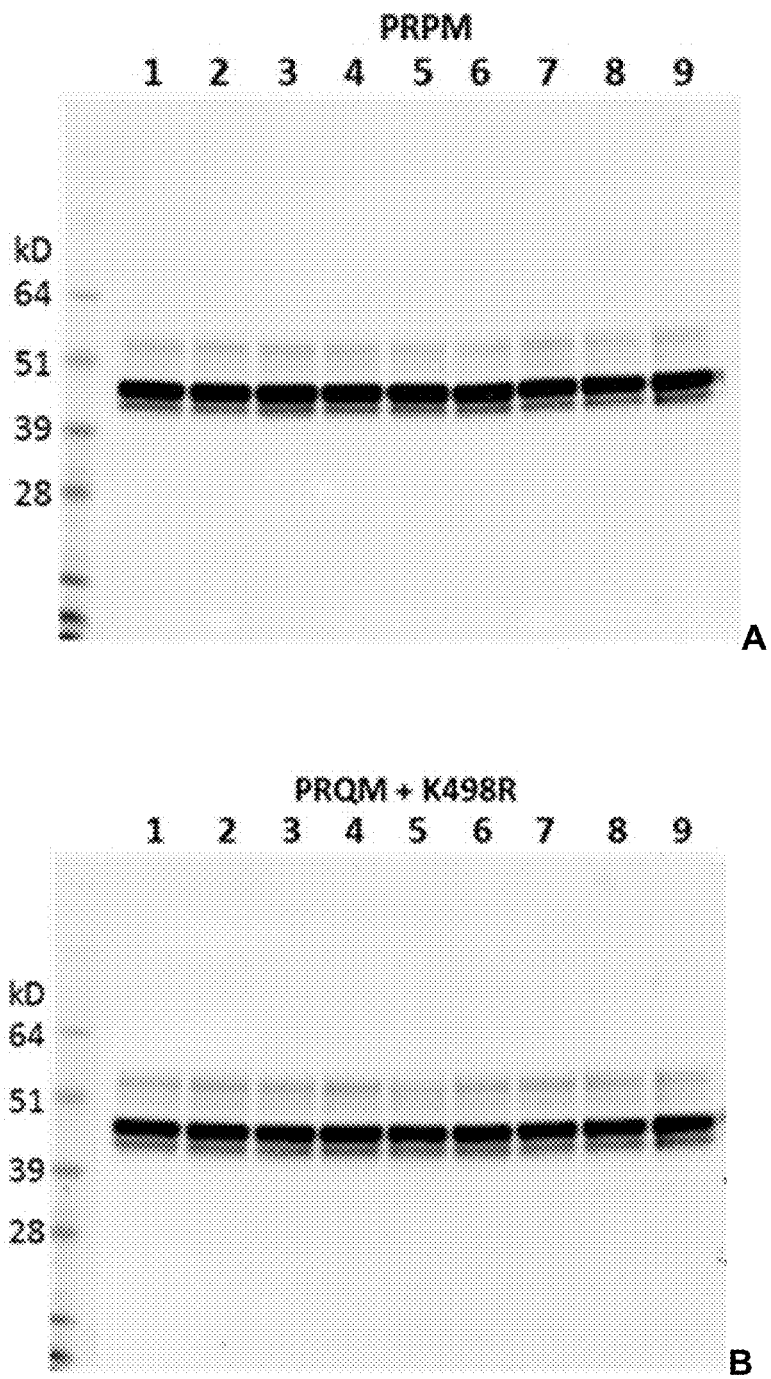
FIG. 6: RSV F proteins of the invention stay intact in CHO cell culture supernatant at pH5. pH of the cell culture supernatants containing F protein variants was adjusted to pH5 and the samples were incubated at 7 days with or without protease inhibitors. The samples were analyzed on SDS-PAGE under reducing conditions. The first lane of each gel is molecular weight standard marker; the size of the standard proteins is indicated. The samples: 1—day 0 sample; 2—day 7 sample incubated at 4° C.; 3—day 7 sample incubated at 4° C. with protease inhibitors; 4—day 0 sample; 5—day 7 sample incubated at room temperature; 6—day 7 sample incubated at room temperature with protease inhibitors; 7—day 0 sample; 8—day 7 sample incubated at 37° C.; 9—day 7 sample incubated at 37° C. with protease inhibitors. In the processed protein samples, the lower band represents the F1 domain and the upper band represents partially processed protein (F1+p27) or unprocessed protein F1+F2). In the single-chain protein sample, the band is F1+F2 domains. PRQM—PR-A2 with N67I, S215P, K66E, and I76V; PRPM—PR-A2 with N67I, S215P, K66E, I76V and D486N. LNR: K683-065.

Five processed proteins were selected for the test. The 5 variants all contained the substitutions K66E, I76V, N67I and S215P. As described above, the latter 2 are required to stabilize the protein in pre-fusion conformation; the former two were included to make the sequence closer to naturally occurring isolates (as was described in the previous section). The proteins differed by the additional mutations E161P, D486N and E487Q. These were chosen because of high expression level, storage stability and low impact on antigenicity. All proteins were expressed in CHO cells and had comparable storage stability. The RSV F proteins were stable in pre-fusion conformation when stored in cell culture supernatants for 2 weeks at 4° C. (FIG. 5). Also, the stability of the RSV F proteins in CHO cell culture supernatant at pH5 was tested. As shown in FIG. 6 no degradation after incubation of protein samples for 7 days at different temperatures was detected.

Figure 7:
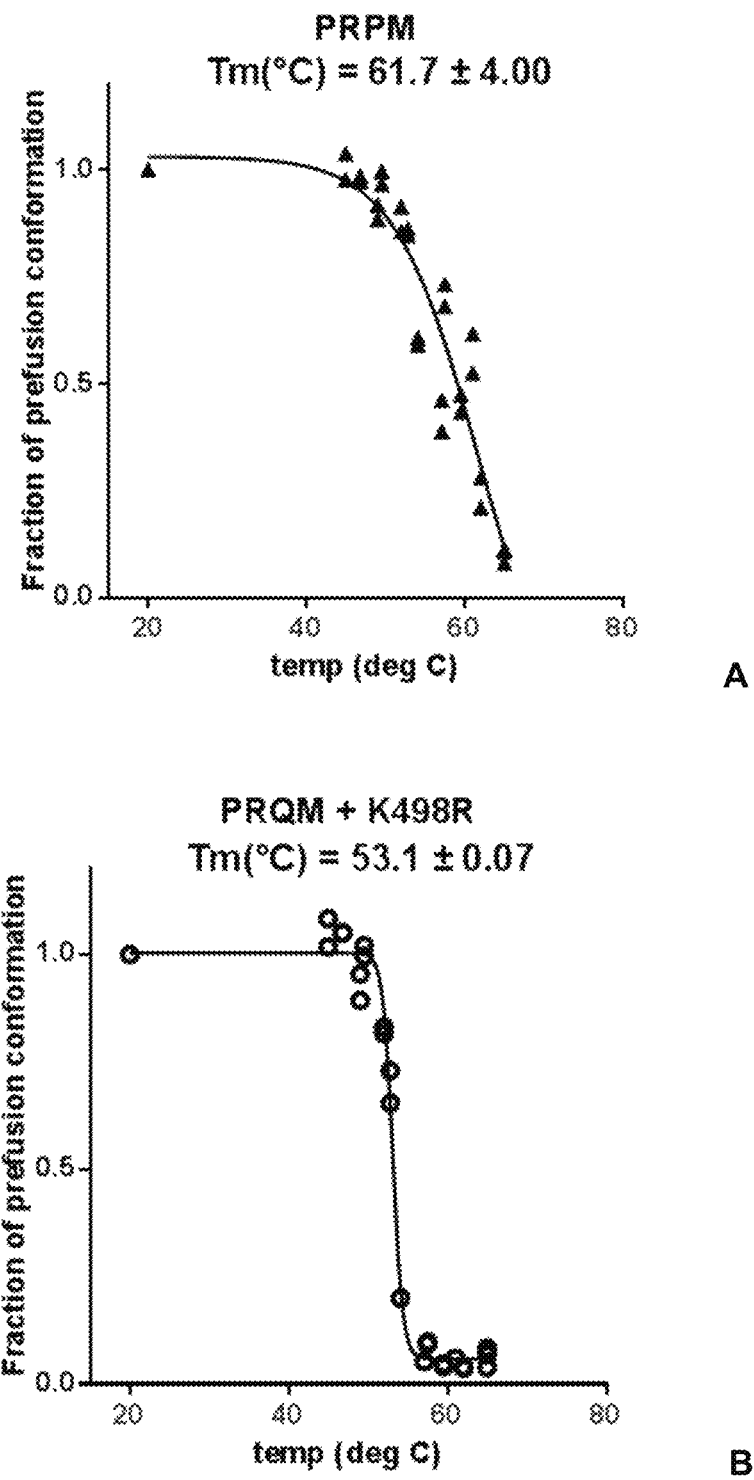
FIG. 7 Temperature stability of RSV F proteins in CHO cell culture supernatant. The supernatant samples were subjected to heat treatment for 30 min at temperatures 45-65° C. The amount of pre-fusion protein in the sample was measured in ELISA with CR9501 antibodies. The values were normalized to untreated sample (20° C.). The curves are shown for each protein individually and an overlay of all curves (on the lower right). Each point represents a replicate measurement. Two assays were performed with 2 technical replicates each. The curves were fitted using Nonlinear regression variable slope equation (GraphPad Prism); melting temperatures (Tm) were calculated as IC50 values. PRQM—PR-A2 with N67I, S215P, K66E, and I76V; PRPM—PR-A2 with N67I, S215P, K66E, I76V and D486N.

In conclusion, the RSV F proteins of the invention expressed in CHO cells and were stable in cell culture supernatants. Additionally, the temperature stability of the protein was tested. The cell culture supernatants were subjected to heat treatment and amount of pre-fusion protein in the samples was measured in ELISA with CR9501 antibody (FIG. 7).

The variant with D486N (PRPM protein) was most stable against temperature stress. Addition of K498R mutation seemed to have no advantage compared to protein with minimal amount of modification (PRQM). The variants with E161P mutation had highest expression levels (data not shown). However the drawback of this amino acid substitution was that the residue 161 is located on the surface of the protein and on the fringe of epitope for CR9501 antibody.

According to the present invention, it thus was shown that the PRPM (RSV F protein with fibritin foldon trimerization domain and with mutations N67I, S215P, K66E, I76V and D486N, SEQ ID NO: 1) and the PRQM (RSV F protein with fibritin foldon trimerization domain and with N67I, S215P, K66E, and I76V, SEQ ID NO: 2) as a processed pre-fusion protein with minimum of required sequence modifications, as well as the PRQM +S46G or PRPM +S46G variant all are stabilized in the pre-fusion conformation and show a high Tm (Table 1). The latter variants with the S46G substitution have a significantly higher expression level.

TABLE 1

| Protein ID | Freeze-thaw stability | Tm (° C.) |
| --- | --- | --- |
| PRQM S46G | Stable for 3 cycles, aggregation after 5 cycles | 56.2 |
| PRPM S46G | Stable for 5 cyles | 63.6 |
| PRPM | Stable for 5 cycles | 65.0 |

Example 2: Immunogenicity and Protection Induced by PRPM with and without Adjuvant An experiment was conducted to determine the immunogenic and prophylactic efficacy of the recombinant PRPM protein in the presence or absence of an adjuvant in a homologous RSV-A2 challenge cotton rat model. The animals were immunized i.m. on day 0 and 28 with 2 doses of PRPM (5 and 0.5 µg), non-adjuvanted or adjuvanted with 100 µg Adjuphos. The animals were challenged on day 49 with $10^5$ (pfu) of RSV A2. Animals were sacrificed 5 days after challenge and titers were measured in lungs and nose.

Figure 8:
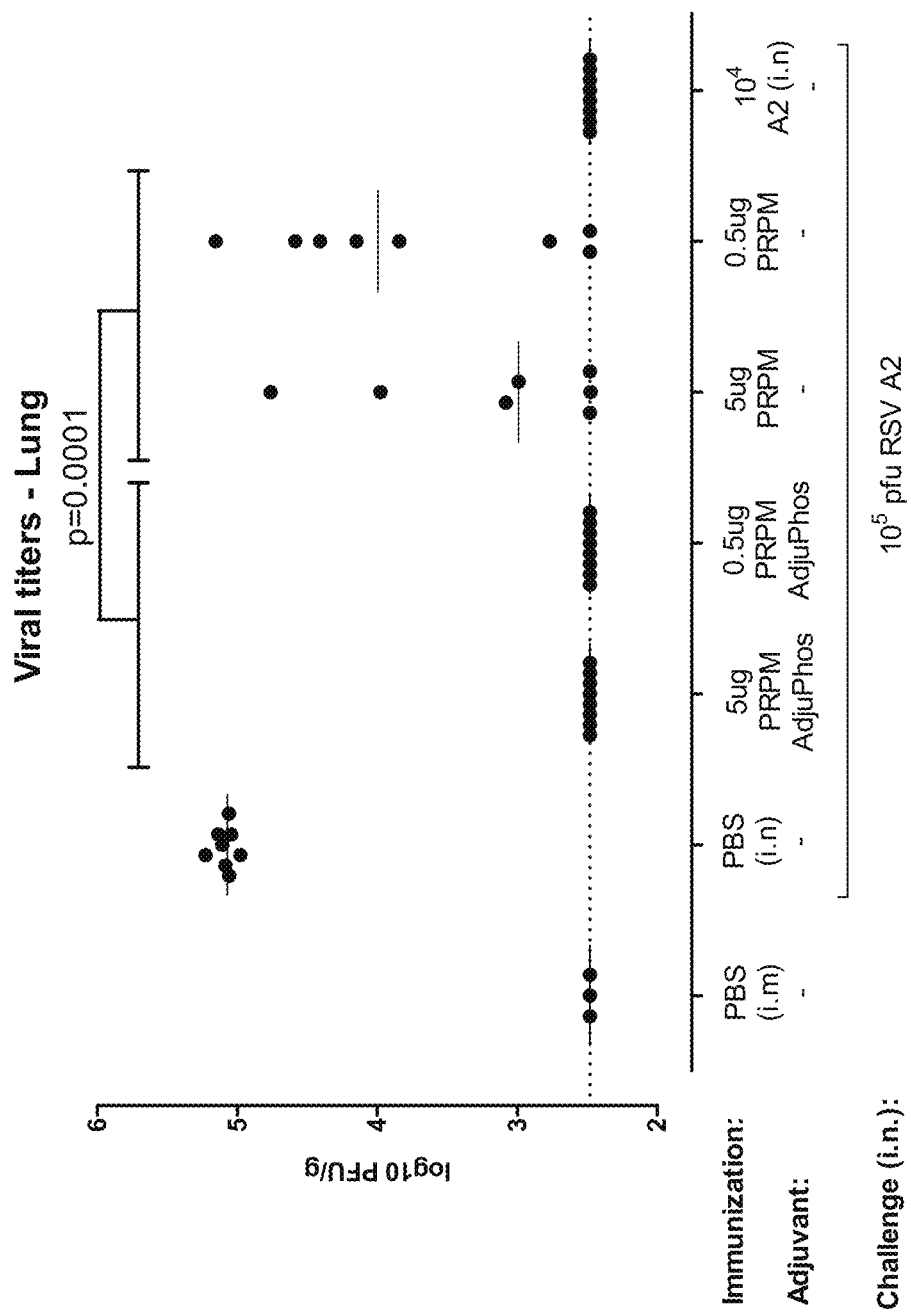
FIG. 8: RSV titers in lungs and nose 5 days after challenge with RSV A2. RSV titers in lungs (upper panel) and nose (lower panel) 5 days after challenge with RSV A2. The lower level of detection (LOD) is indicated by a dotted line. Mean titers (log 10 pfu per gram of tissue) are indicated with horizontal bars. Adjuvanted and non-adjuvanted PRPM groups were compared across dose by a Cochran-Mantel-Haenszel test and statistical differences are indicated in the figure. i.m.: intramuscular; i.n: intranasal.
Figure 9:
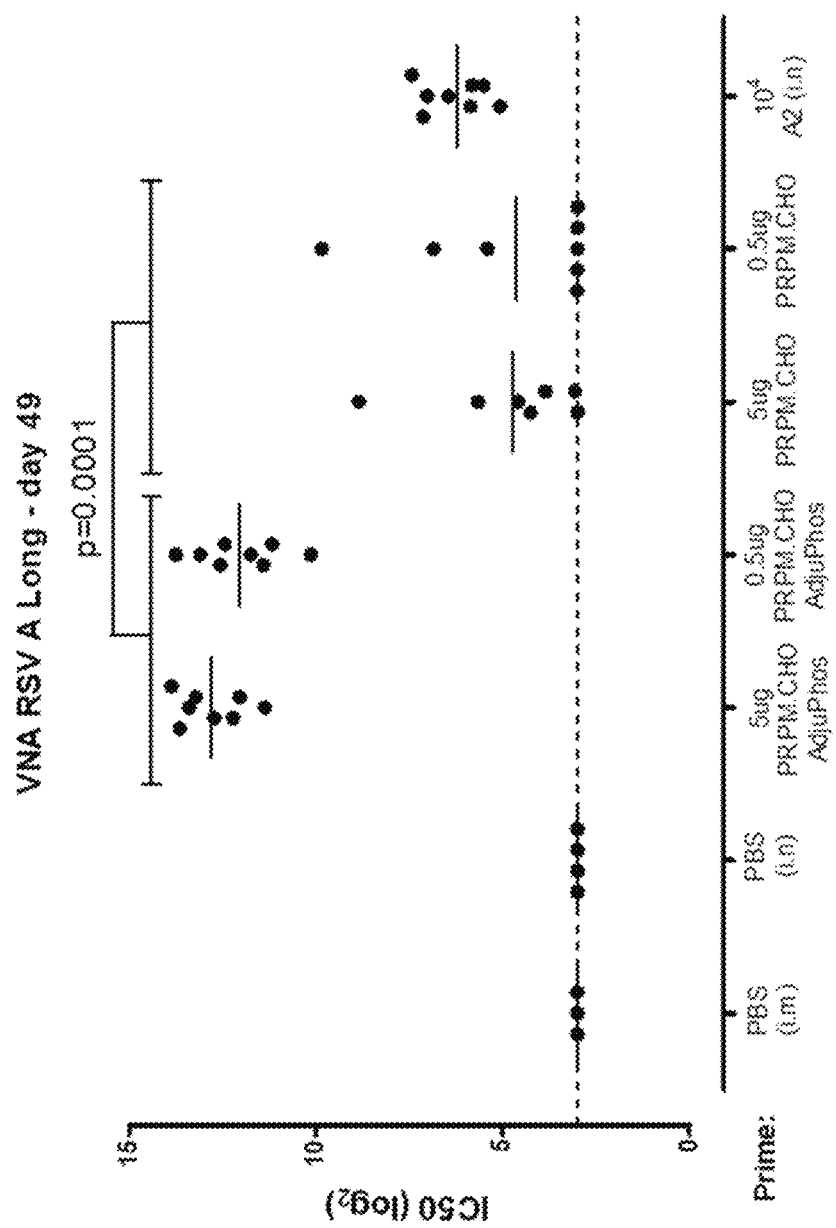
FIG. 9: RSV neutralizing titers against RSV A Long in cotton rats sera at day 49 after priming. RSV neutralizing titers (IC50 (log 2)) against RSV A Long using an ELISA-based readout were determined in cotton rats sera at day 49 after priming. The mean of each group is indicated with a horizontal bar. The limit of detection (LOD) is set on 3.0 (log 2 and indicated with a dashed line). VNA titers induced PRPM by adjuvanted and non-adjuvanted were compared across dose by ANOVA and the results are indicated in the figure. i.m.: intramuscular; i.n: intranasal.

Results immunization with adjuvanted PRPM induced complete protection in the lungs and nose, with the exception of 1 animal that showed breakthrough in the nose. Most of the animals receiving 5 and 0.5 µg non-adjuvanted PRPM showed breakthrough in the lungs and noses and there was a significant difference between the groups receiving the adjuvanted and the non-adjuvanted protein (FIG. 8). The adjuvanted protein induced significantly higher VNA titers compared to the non-adjuvanted protein at day 49 after immunization (FIG. 9).

TABLE 1

Antibody sequences

| Ab | VH domain | VH CDR1 | VH CDR2 | VH CDR3 |
| --- | --- | --- | --- | --- |
| CR9501 | Amino acids 1-125 of SEQ ID NO: 16 | GASINSDNYYWT (SEQ ID NO: 4) | HISYTGNTYYTPSLKS (SEQ ID NO: 5) | CGAYVLISNCGWFDS (SEQ ID NO: 6) |
| CR9502 | Amino acids 1-121 of SEQ ID NO: 18 | GFTFSGHTIA (SEQ ID NO: 10) | WVSTNNGNTEYAQKIQG (SEQ ID NO: 11) | EWLVMGGFAFDH (SEQ ID NO: 12) |

| Ab | VL domain | VL CDR1 | VL CDR2 | VL CDR3 |
| --- | --- | --- | --- | --- |
| CR9501 | Amino acids 1-107 of SEQ ID NO: 17 | QASQDISTYLN (SEQ ID NO: 7) | GASNLET (SEQ ID NO: 8) | QQYQYLPYT (SEQ ID NO: 9) |
| CR9502 | Amino acids 1-110 of SEQ ID NO: 19 | GANNIGSQNVH (SEQ ID NO: 13) | DDRDRPS (SEQ ID NO: 14) | QVWDSSRDQAVI (SEQ ID NO: 15) |

Sequences

SEQ ID NO: 1: PRPM
MELLILKANAITTILTAVTFCFASGQNITEEFYQSTCSAVSKGYLSALRTGWYTSVITIE
LSNI<u>KEI</u>KCNGTDAK<u>V</u>KLIKQELDKYKNAVTELQLLMQSTPATNNRARRELPRFMN
YTLNNAKKTNVTLSKKRKRRFLGFLLGVGSAIASGVAVSKVLHLEGEVNKIKSALLS
TNKAVVSLSNGVSVLTSKVLDLKNYIDKQLLPIVNKQSCSI<u>PN</u>IETVIEFQQKNNRLLE
ITREFSVNAGVTTPVSTYMLTNSELLSLINDMPITNDQKKLMSNNVQIVRQQSYSIMSI
IKEEVLAYVVQLPLYGVIDTPCWKLHTSPLCTTNTKEGSNICLTRTDRGWYCDNAGS
VSFFPQAETCKVQSNRVFCDTMNSLTLPSEVNLCNVDIFNPKYDCKIMTSKTDVSSSV

```
ITSLGAIVSCYGKTKCTASNKNRGIIKTFSNGCDYVSNKGVDTVSVGNTLYYVNKQE
GKSLYVKGEPIINFYDPLVFPSNEFDASISQVNEKINQSLAFIRKSDELLSAIGGYIPEAF
RDGQXYYRKDGEWVLLSTFL

SEQ ID NO: 2 PRQM
MELLILKANAITTILTAVTFCFASGQNITEEFYQSTCSAVSKGYLSALRTGWYTSVITIE
LSNIKEIKCNGTDAKVKLIKQELDKYKNAVTELQLLMQSTPATNNRARRELPRFMN
YTLNNAKKTNVTLSKKRKRRFLGFLLGVGSAIASGVAVSKVLHLEGEVNKIKSALLS
TNKAVVSLSNGVSVLTSKVLDLKNYIDKQLLPIVNKQSCSIPNIETVIEFQQKNNRLLE
ITREFSVNAGVTTPVSTYMLTNSELLSLINDMPITNDQKKLMSNNVQIVRQQSYSIMSI
IKEEVLAYVVQLPLYGVIDTPCWKLHTSPLCTTNTKEGSNICLTRTDRGWYCDNAGS
VSFFPQAETCKVQSNRVFCDTMNSLTLPSEVNLCNVDIFNPKYDCKIMTSKTDVSSSV
ITSLGAIVSCYGKTKCTASNKNRGIIKTFSNGCDYVSNKGVDTVSVGNTLYYVNKQE
GKSLYVKGEPIINFYDPLVFPSDEFDASISQVNEKTNQSLAFIRKSDELLSAIGGYIPEAP
RDGQAYVRKDGEWVLLSTFL

SEQ ID NO: 3 PRPM + S46G
MELLILKANAITTILTAVTFCFASGQNITEEFYQSTCSAVSKGYLGALRTGWYTSVITI
ELSNIKEIKCNGTDAKVKLIKQELDKYKNAVTELQLLMQSTPATNNRARRELPRFMN
YTLNNAKKTNVTLSKKRKRRFLGFLLGVGSAIASGVAVSKVLHLEGEVNKIKSALLS
TNKAVVSLSNGVSVLTSKVLDLKNYIDKQLLPIVNKQSCSIPNIETVIEFQQKNNRLLE
ITREFSVNAGVTTPVSTYMLTNSELLSLINDMPITNDQKKLMSNNVQIVRQQSYSIMSI
IKEEVLAYVVQLPLYGVIDTPCWKLHTSPLCTTNTKEGSNICLTRTDRGWYCDNAGS
VSFFPQAETCKVQSNRVFCDTMNSLTLPSEVNLCNVDIFNPKYDCKIMTSKTDVSSSV
ITSLGAIVSCYGKTKCTASNKNRGIIKTFSNGCDYVSNKGVDTVSVGNTLYYVNKQE
GKSLYVKGEPIINFYDPLVFPSNEFDASISQVNEKINQSLAFIRKSDELLSAIGGYIPEAP
RDGQAYVRKDGEWVLLSTFL

CR9501 heavy chain (SEQ ID NO: 16):
QVQLVQSGPGLVKPSQTLALTCNVSGASINSDNYYWTWIRQRPGGGLEWIGHISYTG
NTYYTPSLKSRLSMSLETSQSQFSLRLTSVTAADSAVYFCAACGAYVLISNCGWFDS
WGQGTQVTVSSASTKGPSVFPLAPSSKSTSGGTAALGCLVKDYFPEPVTVSWNSGAL
TSGVHTFPAVLQSSGLYSLSSVVTVPSSSLGTQTYICNVNHKPSNTKVDKKVEPKSC CR9501 light chain (SEQ ID NO: 17):
EIVMTQSPSSLSASIGDRVTITCQASQDISTYLNWYQQKPGQAPRLLIYGASNLETGVP
SRFTGSGYGTDFSVTISSLQPEDIATYYCQQYQYLPYTFAPGTKVEIKRTVAAPSVFIF
PPSDEQLKSGTASVVCLLNNFYPREAKVQWKVDNALQSGNSQESVTEQDSKDSTYS
LSSTLTLSKADYEKHKVYACEVTHQGLSSPVTKSFNRGEC CR9502 heavy chain (SEQ ID NO:18):
EVQLLQSGAELKKPGASVKISCKTSGFTFSGHTIAWVRQAPGQGLEWMGWVSTNNG
NTEYAQKIQGRVTMTMDTSTSTVYMELRSLTSDDTAVYFCAREWLVMGGFAFDHW
GQGTLLTVSSASTKGPSVFPLAPSSKSTSGGTAALGCLVKDYFPEPVTVSWNSGALTS
GVHTFPAVLQSSGLYSLSSVVTVPSSSLGTQTYICNVNHKPSNTKVDKRVEPKSC CR9502 light chain (SEQ ID NO: 19):
QSVLTQASSVSVAPGQTARITCGANNIGSQNVHWYQQKPGQAPVLVVYDDRDRPSG
IPDUSGSNSGNTATLTISRVEAGDEADYYCQVWDSSRDQAVIFGGGTKLTVLGQPK
AAPSVTLFPPSSEELQANKATLVCLISDFYPGAVTVAWKADSSPVKAGVETTTPSKQS
NNKYAASSYLSLTPEQWKSHRSYSCQVTHEGSTVEKTIAPTECS Nucleotide sequence encoding PRPM (SEQ ID NO: 20):
ATGGAACTGCTGATCCTGAAGGCCAACGCCATCACCACCATCCTGACCGCCGTGACCTTCTGCTTCGCCAGCG
GCCAGAACATCACCGAGGAATTCTACCAGAGCACCTGTAGCGCCGTGTCCAAGGGCTACCTGAGCGCCCTGA
GAACCGGCTGGTACACCAGCGTGATCACCATCGAGCTGAGCAACATCAAGGAAATCAAGTGCAACGGCACCG
ACGCCAAGGTCAAGCTGATCAAGCAGGAACTGGACAAGTACAAGAACGCCGTGACCGAGCTGCAGCTGCTG
ATGCAGAGCACCCCCGCCACCAACAACCGGGCCAGACGCGAGCTGCCCCGGTTCATGAACTACACCCTGAAC
AACGCCAAAAAGACCAACGTGACCCTGAGCAAGAAGCGGAAGCGGCGGTTCCTGGGCTTCCTGCTGGGCGT
GGGCTCTGCCATTGCTAGCGGCGTGGCCGTGTCTAAGGTGCTGCACCTGGAAGGCGAAGTGAACAAGATCAA
GAGCGCCCTGCTGAGCACCAACAAGGCCGTGGTGTCCCTGAGCAACGGCGTGTCCGTGCTGACCAGCAAGGT
GCTGGATCTGAAGAACTACATCGACAAGCAGCTGCTGCCCATCGTGAACAAGCAGAGCTGCAGCATCCCCAA
CATCGAGACAGTGATCGAGTTCCAGCAGAAGAACAACCGGCTGCTGGAAATCACCCGCGAGTTCAGCGTGAA
CGCTGGCGTGACCACCCCCGTGTCCACCTACATGCTGACCAACAGCGAGCTGCTGAGCCTGATCAACGACATG
CCCATCACCAACGACCAGAAAAAGCTGATGAGCAACAACGTGCAGATCGTGCGGCAGCAGAGCTACTCCATC
ATGAGCATCATCAAAGAAGAGGTGCTGGCCTACGTGGTGCAGCTGCCCCTGTACGGCGTGATCGACACCCCC
TGCTGGAAGCTGCACACCAGCCCCTGTGCACCACCAACACCAAAGAGGGCAGCAACATCTGCCTGACCCGG
ACCGACCGGGGCTGGTACTGCGATAATGCCGGCTCCGTGTCATTCTTTCCACAGGCCGAGACATGCAAGGTGC
AGAGCAACCGGGTGTTCTGCGACACCATGAACAGCCTGACCCTGCCCTCCGAAGTGAACCTGTGCAACGTGG
ACATCTTCAACCCCAAGTACGACTGCAAGATCATGACCAGCAAGACCGACGTGTCCAGCTCCGTGATCACCTC
CCTGGGCGCCATCGTGTCCTGCTACGGCAAGACCAAGTGCACCGCCAGCAACAAGAACCGGGGCATCATCAA
GACCTTCAGCAACGGCTGCGACTACGTGTCCAACAAGGGGGTGGACACCGTGTCCGTGGGCAACACCCTGTA
CTACGTGAACAAACAGGAAGGCAAGAGCCTGTACGTGAAGGGCGAGCCCATCATCAACTTCTACGACCCCCT
GGTGTTCCCCAGCAACGAGTTCGACGCCAGCATCAGCCAGGTCAACGAGAAGATCAACCAGAGCCTGGCCTT
CATCAGAAAGAGCGACGAGCTGCTGTCCGCCATCGGCGGCTACATCCCCGAGGCCCCTAGAGATGGCCAGGC
CTACGTGCGGAAGGACGGCGAGTGGGTGCTGCTGTCTACCTTCCTG
```

| Sequences |
|---|
| Nucleotide sequence encoding PRQM (SEQ ID NO: 21):<br>ATGGAACTGCTGATCCTGAAGGCCAACGCCATCACCACCATCCTGACCGCCGTGACCTTCTGCTTCGCCAGCG<br>GCCAGAACATCACCGAGGAATTCTACCAGAGCACCTGTAGCGCCGTGTCCAAGGGCTACCTGAGCGCCCTGA<br>GAACCGGCTGGTACACCAGCGTGATCACCATCGAGCTGAGCAACATCAAGGAAATCAAGTCAACGGCACCG<br>ACGCCAAGGTCAAGCTGATCAAGCAGGAACTGGACAAGTACAAGAACGCCGTGACCGAGCTGCAGCTGCTG<br>ATGCAGAGCACCCCCGCCACCAACAACCGGGCCAGACGCGAGCTGCCCCGGTTCATGAACTACACCCTGAAC<br>AACGCCAAAAAGACCAACGTGACCCTGAGCAAGAAGCGGAAGCGGCGGTTCCTGGGCTTCCTGCTGGGCGT<br>GGGCTCTGCCATTGCTAGCGGCGTGGCCGTGTCTAAGGTGCTGCACCTGGAAGGCGAAGTGAACAAGATCAA<br>GAGCGCCCTGCTGAGCACCAACAAGGCCGTGGTGTCCCTGAGCAACGGCGTGTCCGTGCTGACCAGCAAGGT<br>GCTGGATCTGAAGAACTACATCGACAAGCAGCTGCTGCCCATCGTGAACAAGCAGAGCTGCAGCATCCCCAA<br>CATCGAGACAGTGATCGAGTTCCAGCAGAAGAACAACCGGCTGCTGGAAATCACCCGCGAGTTCAGCGTGAA<br>CGCTGGCGTGACCACCCCCGTGTCCACCTACATGCTGACCAACAGCGAGCTGCTGAGCCTGATCAACGACATG<br>CCCATCACCAACGACCAGAAAAAGCTGATGAGCAACAACGTGCAGATCGTGCGGCAGCAGAGCTACTCCATC<br>ATGAGCATCATCAAGAAGAGGTGCTGGCCTACGTGGTGCAGCTGCCCCTGTACGGCGTGATCGACACCCCC<br>TGCTGGAAGCTGCACACCAGCCCCTGTGCACCACCAACACCAAAGAGGGCAGCAACATCTGCCTGACCCGG<br>ACCGACCGGGGCTGGTACTGCGATAATGCCGGCTCCGTGTCATTCTTTCCACAGGCCGAGACATGCAAGGTGC<br>AGAGCAACCGGGTGTTCTGCGACACCATGAACAGCCTGACCCTGCCCTCCGAAGTGAACCTGTGCAACGTGG<br>ACATCTTCAACCCTAAGTACGACTGCAAGATCATGACCAGCAAGACCGACGTGTCCAGCTCCGTGATCACCTC<br>CCTGGGCGCCATCGTGTCCTGCTACGGCAAGACCAAGTGCACCGCCAGCAACAAGAACCGGGGCATCATCAA<br>GACCTTCAGCAACGGCTGCGACTACGTGTCCAACAAGGGGGTGGACACCGTGTCCGTGGGCAACACCCTGTA<br>CTACGTGAACAAACAGGAAGGCAAGAGCCTGTACGTGAAGGGCGAGCCCATCATCAACTTCTACGACCCCCT<br>GGTGTTCCCCAGCGACGAGTTCGACGCCAGCATCAGCCAGGTCAACGAGAAGATCAACCAGAGCCTGGCCTT<br>CATCAGAAAGAGCGACGAGCTGCTGTCCGCCATCGGCGGCTACATCCCCGAGGCCCCTAGAGATGGCCAGGC<br>CTACGTGCGGAAGGACGGCGAGTGGGTGCTGCTGTCTACCTTCCTG |
| Nucleotide sequence encoding PRPM + S46G (SEQ ID NO: 22):<br>ATGGAACTGCTGATCCTGAAGGCCAACGCCATCACCACCATCCTGACCGCCGTGACCTTCTGCTTTGCCAGCG<br>GCCAGAACATCACCGAGGAATTCTACCAGAGCACCTGTAGCGCCGTGTCCAAGGGCTACCTGAGCGCCCTGA<br>GAACCGGCTGGTACACCAGCGTGATCACCATCGAGCTGAGCAACATCAAAGAAATCAAGTCAACGGCACCG<br>ACGCCAAAGTGAAGCTGATCAAGCAGGAACTGGACAAGTACAAGAATGCCGTGACCGAACTGCAGCTGCTGA<br>TGCAGAGCACCCCCGCCACCAACAACCGGGCCAGAAGAGAACTGCCCAGATTCATGAACTACACCCTGAACA<br>ACGCCAAAAAGACCAACGTGACCCTGAGCAAGAAGCGGAAGCGGCGGTTCCTGGGCTTTCTGCTGGGAGTG<br>GGAAGCGCCATTGCTAGCGGAGTGGCCGTGTCTAAGGTGCTGCACCTGGAAGGCGAAGTGAACAAGATCAA<br>GAGCGCCCTGCTGAGCACCAACAAGGCCGTGGTGTCTCTGAGCAACGGCGTGTCCGTGCTGACCAGCAAGGT<br>GCTGGATCTGAAGAACTACATCGACAAACAGCTGCTGCCCATCGTGAACAAGCAGAGCTGCAGCATCCCCAAC<br>ATCGAGACAGTGATCGAGTTCCAGCAGAAGAACAACCGGCTGCTGGAAATCACCCGCGAGTTCAGCGTGAAC<br>GCTGGCGTGACCACCCCCGTGTCCACCTACATGCTGACCAACAGCGAGCTGCTGTCCCTGATCAACGACATGC<br>CCATCACCAACGACCAGAAAAAGCTGATGAGCAACAACGTGCAGATCGTGCGGCAGCAGAGCTACTCCATCA<br>TGAGCATTATCAAAGAAGAGGTGCTGGCCTACGTGGTGCAGCTGCCTCTGTACGGCGTGATCGACACCCCCTG<br>CTGGAAGCTGCACACCAGCCCTCTGTGCACCACCAACACCAAAGAGGGCAGCAACATCTGCCTGACCCGGACC<br>GACAGAGGCTGGTACTGCGATAATGCCGGCTCCGTCTCATTCTTTCCACAAGCCGAGACATGCAAGGTGAAC<br>GCAACCGGGTGTTCTGCGACACCATGAACAGCCTGACCCTGCCCTCCGAAGTGAATCTGTGCAACGTGGACAT<br>CTTCAACCCTAAGTACGACTGCAAGATCATGACCTCCAAGACCGACGTGTCCAGCTCCGTGATCACAAGCCTG<br>GGCGCCATCGTGTCCTGCTACGGCAAGACCAAGTGCACCGCCAGCAACAAGAACCGGGGCATCATCAAGACC<br>TTCAGCAACGGCTGCGACTACGTGTCCAACAAGGGGGTGGACACCGTGTCTGTGGGCAACACCCTGTACTAC<br>GTGAACAAACAGGAAGGCAAGAGCCTGTACGTGAAGGGCGAGCCCATCATCAACTTCTACGACCCCCTGGTG<br>TTCCCCAGCAACGAGTTCGACGCCAGCATCAGCCAAGTGAACGAGAAGATCAACCAGAGCCTGGCMCATCA<br>GAAAGTCCGATGAGCTGCTGAGCGCCATCGGCGGCTACATCCCTGAGGCCCCTAGAGATGGCCAGGCCTATG<br>TGCGGAAGGACGGCGAATGGGTGCTGCTGTCTACCTTTCTG |

The invention claimed is:

1. A nucleic acid molecule encoding a recombinant prefusion respiratory syncytial virus (RSV) Fusion (F) protein, the nucleic acid molecule comprising a nucleotide sequence selected from the group consisting of SEQ ID NO: 20, SEQ ID NO: 21, and SEQ ID NO: 22.

2. The nucleic acid molecule according to claim 1, wherein the nucleic acid molecule comprises the nucleotide sequence of SEQ ID NO: 20.

3. A vector comprising the nucleic acid molecule according to claim 2.

4. A composition comprising the nucleic acid molecule according to claim 2.

5. A method of inducing an immune response against RSV F protein in a subject in need thereof, the method comprising administering to the subject the composition according to claim 4.

6. A method of prophylaxis and/or treatment of RSV infection in a subject in need thereof, the method comprising administering to the subject the composition according to claim 4.

7. A vaccine against RSV comprising the nucleic acid molecule according to claim 2.

8. The nucleic acid molecule according to claim 1, wherein the nucleic acid molecule comprises the nucleotide sequence of SEQ ID NO: 21.

9. A vector comprising the nucleic acid molecule according to claim 8.

10. A composition comprising the nucleic acid molecule according to claim 8.

11. A method of inducing an immune response against RSV F protein in a subject in need thereof, the method comprising administering to the subject the composition according to claim 10.

12. A method of prophylaxis and/or treatment of RSV infection in a subject in need thereof, the method comprising administering to the subject the composition according to claim 10.

13. A vaccine against RSV comprising the nucleic acid molecule according to claim 8.

14. The nucleic acid molecule according to claim 1, wherein the nucleic acid molecule comprises the nucleotide sequence of SEQ ID NO: 22.

15. A vector comprising the nucleic acid molecule according to claim 14.

16. A composition comprising the nucleic acid molecule according to claim 14.

17. A method of inducing an immune response against RSV F protein in a subject in need thereof, the method comprising administering to the subject the composition according to claim 16.

18. A method of prophylaxis and/or treatment of RSV infection in a subject in need thereof, the method comprising administering to the subject the composition according to claim 16.

19. A vaccine against RSV comprising the nucleic acid molecule according to claim 14.

* * * * *

UNITED STATES PATENT AND TRADEMARK OFFICE
CERTIFICATE OF CORRECTION

PATENT NO.        : 11,155,583 B2
APPLICATION NO.   : 16/091344
DATED             : October 26, 2021
INVENTOR(S)       : Anders Krarup et al.

It is certified that error appears in the above-identified patent and that said Letters Patent is hereby corrected as shown below:

In the Specification

Column 7, Line 16, should be corrected as follows:
prise a nucleotide sequence of SEQ ID NO. 20, 21 or 22.

Column 12, Line 2, should be corrected as follows:
23), linked to the amino acid residue 495 of the RSV A2 F1

Signed and Sealed this
Seventh Day of December, 2021

Drew Hirshfeld
*Performing the Functions and Duties of the*
*Under Secretary of Commerce for Intellectual Property and*
*Director of the United States Patent and Trademark Office*